(12) United States Patent
Ober et al.

(10) Patent No.: US 8,930,404 B2
(45) Date of Patent: Jan. 6, 2015

(54) SYSTEM AND METHOD FOR ANALYZING DE-IDENTIFIED HEALTH CARE DATA

(71) Applicant: IMS Health Incorporated, Danbury, CT (US)

(72) Inventors: N. Stephen Ober, Southboro, MA (US);
John Grubmuller, Bedford, NH (US);
Maureen Farrell, Bedford, MA (US);
Charles Wentworth, Attleboro, MA (US); Thomas Gilbert, Holliston, MA (US); Kevin Barrett, Sherborn, MA (US); Steven Davis, Brookline, MA (US); Erik Nordman, Waltham, MA (US); Randell Grenier, Waltham, MA (US)

(73) Assignee: IMS Health Incorporated, Danbury, CT (US)

( * ) Notice: Subject to any disclaimer, the term of this patent is extended or adjusted under 35 U.S.C. 154(b) by 0 days.

(21) Appl. No.: 13/925,243

(22) Filed: Jun. 24, 2013

(65) Prior Publication Data
US 2014/0040308 A1 Feb. 6, 2014

Related U.S. Application Data

(63) Continuation of application No. 09/665,752, filed on Sep. 20, 2000, now Pat. No. 8,473,452.

(60) Provisional application No. 60/154,726, filed on Sep. 20, 1999.

(51) Int. Cl.
| *G06F 17/30* | (2006.01) |
| *G06Q 10/10* | (2012.01) |
| *G06F 19/00* | (2011.01) |
| *G06F 21/62* | (2013.01) |

(52) U.S. Cl.
CPC ............... *G06F 19/32* (2013.01); *G06Q 10/10* (2013.01); *G06F 19/322* (2013.01); *G06F 17/30592* (2013.01); *G06F 21/6254* (2013.01); *G06F 19/3456* (2013.01); *G06F 19/326* (2013.01)

USPC .......... 707/790; 707/607; 707/609; 707/687; 707/813; 707/821

(58) Field of Classification Search
USPC .................. 707/607, 609, 687, 790, 813, 821
See application file for complete search history.

(56) References Cited

U.S. PATENT DOCUMENTS

| 3,752,904 A | 8/1973 | Waterbury |
| 3,896,266 A | 7/1975 | Waterbury |

(Continued)

FOREIGN PATENT DOCUMENTS

| EP | 869637 A3 | 12/2000 |
| EP | 1026603 A3 | 1/2002 |

(Continued)

OTHER PUBLICATIONS

Chaudhuri Set al: "An Overview of Data Warehousing and OLAP Technology" Sigmod Record, Sigmod, New York, NY, US, vol. 26, No. 1, Mar. 1997, pp. 65-74, XP002193792, ISSN: 0163-5808.

(Continued)

*Primary Examiner* — Sana Al Hashemi
(74) *Attorney, Agent, or Firm* — Fish & Richardson P.C.

(57) ABSTRACT

A system and method for creating a unique alias associated with an individual identified in a health care database such that health care data, and particularly pharmaceutical-related data, can be efficiently gathered and analyzed. The system has a first data store for storing at least one record where each record includes a plurality of identification fields which when concatenated uniquely identify an individual, and at least one health care field corresponding to health care data associated with the individual. The system also has a second data store, and a processor. The processor selects a record of the first data store, then selects a subset of the plurality of identification fields within the selected record, and concatenates the selected subset of identification fields. Then the processor stores the concatenated identification fields in a record in the second data store with the at least one health care field from the selected record of the first data store.

12 Claims, 17 Drawing Sheets

(56) References Cited

U.S. PATENT DOCUMENTS

| | | | |
|---|---|---|---|
| 4,979,832 A | 12/1990 | Ritter | |
| 4,993,068 A | 2/1991 | Piosenka et al. | |
| 5,003,539 A | 3/1991 | Takemoto et al. | |
| 5,005,200 A | 4/1991 | Fischer | |
| 5,070,452 A | 12/1991 | Doyle, Jr. et al. | |
| 5,214,702 A | 5/1993 | Fischer | |
| 5,299,121 A | 3/1994 | Brill et al. | |
| 5,301,105 A | 4/1994 | Cummings, Jr. | |
| 5,325,290 A | 6/1994 | Cauffman et al. | |
| 5,371,797 A | 12/1994 | Bocinsky, Jr. | |
| 5,471,382 A | 11/1995 | Tallman et al. | |
| 5,502,764 A | 3/1996 | Naccache | |
| 5,581,749 A | 12/1996 | Hossain et al. | |
| 5,606,610 A | 2/1997 | Johansson | |
| 5,644,778 A | 7/1997 | Burks et al. | |
| 5,652,842 A | 7/1997 | Siegrist, Jr. et al. | |
| 5,664,109 A | 9/1997 | Johnson et al. | |
| 5,666,492 A | 9/1997 | Rhodes et al. | |
| 5,704,044 A | 12/1997 | Tarter et al. | |
| 5,724,575 A | 3/1998 | Hoover et al. | |
| 5,754,938 A | 5/1998 | Herz et al. | |
| 5,758,085 A | 5/1998 | Kouoheris et al. | |
| 5,758,095 A | 5/1998 | Albaum et al. | |
| 5,787,186 A | 7/1998 | Schroeder | |
| 5,793,969 A | 8/1998 | Kamentsky et al. | |
| 5,799,086 A | 8/1998 | Sudia | |
| 5,799,308 A | 8/1998 | Dixon | |
| 5,821,871 A | 10/1998 | Benzler | |
| 5,823,948 A | 10/1998 | Ross, Jr. et al. | |
| 5,825,906 A | 10/1998 | Obata et al. | |
| 5,832,449 A | 11/1998 | Cunningham | |
| 5,867,821 A | 2/1999 | Ballantyne et al. | |
| 5,876,926 A | 3/1999 | Beecham | |
| 5,890,129 A | 3/1999 | Spurgeon | |
| 5,907,677 A | 5/1999 | Glenn et al. | |
| 5,915,240 A | 6/1999 | Karpf | |
| 5,918,208 A | 6/1999 | Javitt | |
| 5,920,854 A | 7/1999 | Kirsch et al. | |
| 5,925,810 A | 7/1999 | McBroom | |
| 5,956,716 A | 9/1999 | Kenner et al. | |
| 5,961,593 A | 10/1999 | Gabber et al. | |
| 5,970,462 A | 10/1999 | Reichert | |
| 5,991,731 A | 11/1999 | Colon et al. | |
| 5,995,939 A | 11/1999 | Berman et al. | |
| 6,003,006 A | 12/1999 | Colella et al. | |
| 6,012,051 A | 1/2000 | Sammon, Jr. et al. | |
| 6,014,631 A | 1/2000 | Teagarden et al. | |
| 6,018,713 A | 1/2000 | Coli et al. | |
| 6,024,287 A | 2/2000 | Takai et al. | |
| 6,079,021 A | 6/2000 | Abadi et al. | |
| 6,085,322 A | 7/2000 | Romney et al. | |
| 6,249,768 B1 | 6/2001 | Tulskie, Jr. et al. | |
| 6,266,675 B1* | 7/2001 | Evans et al. | 1/1 |
| 6,302,844 B1* | 10/2001 | Walker et al. | 600/300 |
| 6,317,700 B1 | 11/2001 | Bagne | |
| 6,341,267 B1 | 1/2002 | Taub | |
| 6,397,224 B1 | 5/2002 | Zubeldia et al. | |
| 6,421,650 B1* | 7/2002 | Goetz et al. | 705/3 |
| 6,449,621 B1 | 9/2002 | Pettovello | |
| 6,496,931 B1 | 12/2002 | Rajchel et al. | |
| 6,654,724 B1 | 11/2003 | Rubin et al. | |
| 6,732,113 B1 | 5/2004 | Ober et al. | |
| 6,734,886 B1 | 5/2004 | Hagan et al. | |
| 6,915,265 B1 | 7/2005 | Johnson | |
| 7,184,947 B2 | 2/2007 | Matsuoka et al. | |
| 7,200,578 B2 | 4/2007 | Paltenghe et al. | |
| 7,309,001 B2 | 12/2007 | Banfield et al. | |
| 7,346,521 B2 | 3/2008 | Tolle et al. | |
| 7,376,677 B2 | 5/2008 | Ober et al. | |
| 7,386,526 B1 | 6/2008 | Chappel | |
| 7,428,706 B2 | 9/2008 | Hagan et al. | |
| 7,865,376 B2 | 1/2011 | Ober et al. | |
| 8,473,452 B1 | 6/2013 | Ober et al. | |
| 2002/0073138 A1 | 6/2002 | Gilbert et al. | |
| 2002/0198473 A1 | 12/2002 | Kumar et al. | |
| 2003/0097358 A1 | 5/2003 | Mendez | |
| 2004/0088355 A1 | 5/2004 | Hagan et al. | |
| 2004/0199781 A1 | 10/2004 | Erickson et al. | |
| 2004/0215981 A1 | 10/2004 | Ricciardi et al. | |
| 2005/0027564 A1 | 2/2005 | Yantis | |
| 2005/0065912 A1 | 3/2005 | Cafrelli et al. | |
| 2005/0114334 A1 | 5/2005 | Ober et al. | |
| 2005/0165623 A1 | 7/2005 | Landi et al. | |
| 2005/0234740 A1 | 10/2005 | Krishnan et al. | |
| 2005/0236474 A1 | 10/2005 | Onuma et al. | |
| 2005/0256740 A1 | 11/2005 | Kohan et al. | |
| 2005/0256741 A1 | 11/2005 | Kohan et al. | |
| 2005/0256742 A1 | 11/2005 | Kohan et al. | |
| 2005/0268094 A1 | 12/2005 | Kohan et al. | |
| 2006/0026156 A1 | 2/2006 | Zuleba | |
| 2008/0091474 A1 | 4/2008 | Ober et al. | |
| 2008/0147554 A1 | 6/2008 | Stevens et al. | |
| 2010/0114607 A1 | 5/2010 | Kress et al. | |

FOREIGN PATENT DOCUMENTS

| | | |
|---|---|---|
| JP | 6083847 B | 10/1994 |
| JP | H1021302 A | 1/1998 |
| JP | 10254807 A | 9/1998 |
| JP | 2000513463 T | 10/2000 |
| JP | 2000514938 T | 11/2000 |
| JP | 2007056989 A | 3/2007 |
| JP | 2008147364 A | 6/2008 |
| JP | 2010232811 A | 10/2010 |
| JP | 2011525614 A | 9/2011 |
| JP | 2011250165 A | 12/2011 |
| JP | 2011238064 A5 | 6/2013 |
| WO | WO9515628 A1 | 6/1995 |
| WO | WO9641275 A1 | 12/1996 |
| WO | WO9642059 A1 | 12/1996 |
| WO | WO9802837 A1 | 1/1998 |
| WO | WO0077642 A1 | 12/2000 |
| WO | WO0118631 A1 | 3/2001 |
| WO | WO2007145010 A1 | 12/2007 |

OTHER PUBLICATIONS

Brannigan V M and Beier B R: "Patient privacy in the era of medical computer networks: a new paradigm for a new technology." Proceedings of the Eighth World Congress on Medical Informatics, vol. 8, No. 1, Jul. 23, 1995-Jul. 27, 1995 pp. 640-643, XP009040274, Vancouver, British Columbia, Canada, ISSN: 1569-6332.

Quantin C et al: "How to ensure data security of an epidemiological follow-up: quality assessment of an anonymous record linkage procedure" International Journal of Medical Informatics, Elsevier Scientific Publishers, Shannon, IR, vol. 49, No. 1, Mar. 1998, pp. 117-122, XP004149470, ISSN: 1386-5056.

Anderson R J: "A security policy model for clinical information systems" Security and Privacy, 1996. Proceedings., 1996 IEEE Symposium on Oakland, CA, USA May 6-8, 1996, Los Alamitos, CA, USA, IEEE Comput. Soc, US, May 6, 1996, pp. 30-43, XPOI064923, ISBN: 0-8186-7417-2.

Supplementary European Search Report dated Nov. 24, 2004 from EP 00 96 5216, 2 pages.

International Search Report dated Jan. 9, 2001 from PCT/US00/25818, 1 page.

J.D. Halamka, P. Szolovits, D. Rind, and C. Safran, A WWW Implementation of National Recommendations for Protecting Electronic Health Information, Journal of the American Medical Informatics Association, vol. 4, No. 6, Nov./Dec. 1997, pp. 458-464.

R. Anderson, The DeCODE Proposal for an Icelandic Health Database, Oct. 20, 1998, pp. 1-12, www.decode.is.

H. Bouzelat, C. Quantin and L. Dusserre, Extraction and Anonymity Protocol of Medical File, Proceedings of the American Medical Informatics Association Annual Fall Symposium, 1996, pp. 323-327, AMIA, Inc.

K.R. Iversen and T.O. Grotan, Socio-technical aspects of the use of health related personal information for management and research, International Journal of Bio-Medical Computing, vol. 43, 1996, pp. 83-91, Elsevier Science Ireland Ltd.

(56) References Cited

OTHER PUBLICATIONS

A. Ohm and L. Ohno-Machado, Using Boolean reasoning to anonymize databases, Artificial Intelligence in Medicine, vol. 15, 1999, pp. 235-254, Elsevier Science B.Y.
K. Kahl, G. Dickson, J. Kebisek and M. Powell, Bar code tracking system enhances record-and film-handling productivity, Top Health Rec Manage, vol. 12, No. 3, Mar. 1992, 1 pg., St.. Joseph's Hospital, Milwaukee, WI, PubMed-indexed for MEDLINE.
E. T. Carroll, S. Wright, and C. Zakoworotny, Securely Implementing Remote Access within Health Information Management, Journal of ANIMA, vol. 69, No. 3, Mar. 1995, pp. 46-49, copied from the National Library of Medicine.
Unique Health Identifier for Individuals, U.S. Department of Health and Human Services, A White Paper, pp. 1-32, http://epic.org/privacy/medical/hhs-id-798.html.
Secure Hash Standard, National Institute of Standards and Technology, Aug. 1, 2002, pp. i-iv and 1-79, Federal Information Processing Standards Publication ISO-2 (+Change Notice to include SHA-224).
English Translation of Japanese Office Action for co-pending application, Reference No. B025547, Mailing No. 571403, Mailing Date: Aug. 10, 2010, Patent Application No. 2001-525614.
Why Clearinghouses Transmit Electronic Claims to Insurance Carriers, and Why the Service They Provide is Essential to Medical Practices, Electronic Claim Clearinghouses, MPM Soft, Practice Billing Software, pp. 1-7, www.mpmsoft.com/EDI/clearinghouse.htm, printed Jan. 5, 2009.
Physicians Who Perform Medical Procedures, From Direct Medical Data, 1 pg., www.DMDdata.com. 2010.
Physicians Treating Patients by Diagnostic Treatement Code ICD9, From Direct Medical Data, 1 pg., www.DMDdata.com, 2008.
U.S. Patent and Trademark Office, Office Action for U.S. Appl. No. 09/665,752, May 5, 2004, 5 pgs.
U.S. Patent and Trademark Office, Office Action for U.S. Appl. No. 09/665,752, Mar. 4, 2005, 6 pgs.
U.S. Patent and Trademark Office, Office Action for U.S. Appl. No. 09/665,752, Dec. 16, 2005, 4 pgs.
U.S. Patent and Trademark Office, Office Action for U.S. Appl. No. 09/665,752, Mar. 16, 2007, 7 pgs.
U.S. Patent and Trademark Office, Office Action for U.S. Appl. No. 09/665,752, Jan. 25, 2008, 7 pgs.
U.S. Patent and Trademark Office, Office Action for U.S. Appl. No. 09/665,752, Dec. 8, 2008, 8 pgs.
X. Thirion, R. Sambuc & J.L. San Marco, Epidemiology and anonymity: a new method, Rev. Epidém. Et. Santé Publ., 1988, pp. 36-42.
Dussere L., Quantin Co. & Bouzelat H., A One Way Public Key Cryptosystem for the Linkage of Nominal Files in Epidemiological Studies, Proceedings of the Eighth World Congress on Med. Informatics, 1995, pp. 644-647.
U.S. Patent and Trademark Office, Notice of Allowance for U.S. Appl. No. 09/665,752, Feb. 27, 2013, 13 pgs.

\* cited by examiner

SYSTEM AND METHOD FOR ANALYZING DE-IDENTIFIED HEALTH CARE DATA

CROSS-REFERENCE TO RELATED APPLICATIONS

This application is a continuation of and claims priority to U.S. application Ser. No. 09/665,752, filed on Sep. 20, 2000, which application claims the benefit of U.S. Provisional Application No. 60/154,726, filed Sep. 20, 1999, the entireties of which applications are incorporated herein by reference.

BACKGROUND OF THE INVENTION

1. Field of the Invention

The present invention generally relates to computer systems and databases. More particularly, the present invention relates to a system and method for the gathering and analysis of health-care related data, and specifically the gathering and analysis of information regarding the use of pharmaceuticals by individuals. The present invention also relates to techniques for de-identifying the individuals from such pharmaceutical data, in order to maintain privacy.

2. Description of the Related Art

In the medical information field, pharmaceutical claims are processed on large computer systems which receive claims data for patients who have been prescribed one or more medications and have filed claims with insurance companies (or government entities) in order to have the claim paid by the company or entity. The claims data includes very specific details and attributes about the individuals making the claims. For example, attributes can include name, gender, birth date, address, medical diagnosis, specific drug prescribed, and other drugs the patient is using. Consequently, this data is very useful in assisting marketing research relative to usage of a specific drug and identifying various attributes that impact the usage.

The claims data is typically received at a data "clearinghouse" which can be a database for a specific insurance company or a larger database providing the claim processing service for many insurance companies. Moreover, the claims data that are produced by claimants include a significant amount of data, with millions of new claims being entered into the system each month. Several of the claims data clearinghouses have systems handling many terabytes of claims data. Because of the large size of the data being produced and the large amount of attributes, the data is in an inadequate format for efficient search, retrieval and analysis of specific attributes.

Recently, there have been laws passed that prevent the transmission of personal information associated with individuals, within health care claims data. This legislation particularly prohibits the transfer of specific personal data such as names, addresses and social security numbers. Thus, the claims data is no longer allowed to be transmitted from the clearinghouse to others in raw form with the personal data. Without the personal information to segregate the claims data, it becomes much harder to generate valuable research and market data based upon the unique attributes for specific individuals, such as age, gender and geographic distribution.

It is therefore desirous to provide the ability to efficiently gather information from the claims databases to allow research and analysis of the attributes that effect the pharmaceutical industry. Accordingly, the present invention is primarily directed to systems and methods for overcoming the problems discussed above, as well as related limitations of the prior art.

SUMMARY OF THE INVENTION

In one embodiment, the present invention is directed to a system and method for creating a unique alias associated with an individual identified in a health care database, that allows the aggregation of segregated data for marketing research. The system may include a first data store for storing at least one record where each record has a plurality of identification fields, such as name and birth date, which when concatenated uniquely identify an individual, and at least one health care field corresponding to health care data associated with the individual, such as a medication type. The system may also have a second data store and a processor that selects a record of the first data store, selects a subset of the plurality of identification fields within the selected record, concatenates the selected subset of identification fields, and stores the concatenated identification fields in a record in the second data store along with at least one health care field from the selected record of the first data store. The first data store and the second data store can either be located within the same database or in separate databases.

The health care data stored within the first data store may, in one embodiment, correspond to pharmaceutical claims data. The selected subset may correspond to a specific person in the healthcare database, and the person's last name, birthday, and gender are concatenated to form a unique identifier for that record. The processor may analyze longitudinal and historical records of individuals using individual-level linking methodologies based on the concatenated identification fields and the at least one health care field of each record of the second data store. The health care data also can have personal data removed from the various records such that only medically significant information remains, and the identifier allows the medical information to be segregated such that the individual records are still identifiable.

In order to more efficiently process the tremendous amount of data of the health care records, the processor may perform the further steps of selectively gathering the records from the first data store and selectively manipulating the records into a data cube. The records of the first data store are typically in tabular form, and the process of manipulating the records comprises selectively joining and projecting records from the various tabular records in the first data store to ultimately form a data cube comprised of a table of records. The data cube format allows the processor to more easily perform a search of the health care records, and also generate a report by displaying the records 25 of a specific data cube.

The present invention thus provides a method for creating a unique alias associated with an individual identified in a health care database, wherein the health care database stores at least one record, and each record has a plurality of identification fields which when taken together uniquely identify an individual, and at least one health care field may correspond to health care data associated with the individual. The method includes the steps of selecting a record within the health care database, selecting a subset of the plurality of identification fields within the selected record, concatenating the selected subset of identification fields, and storing the concatenated identification fields in a record in a second database with the at least one health care field from the selected record of the first data store. The method preferably includes the step of analyzing longitudinal, historical records of individuals using individual level linking methodologies based on the concatenated identification fields and the at least one health care field of each record of the second database.

The step of selecting a record within the health care database may comprise selecting a record from pharmaceutical claims data. Further, the step of concatenating the selected subset of identification fields may comprise, for example, concatenating, for a specific person in the healthcare database, that person's last name, birthday, and gender. Thus, based on the concatenated identification fields and the at least one health care field of each record of the second data store, the method may include the step of analyzing longitudinal, historical records of individuals using individual-level linking methodologies.

As discussed above, the method further may include the steps of selectively gathering the records from the first data store, and selectively manipulating the records into a data cube. The step of selecting a record within the health care database may comprise selecting records of the first data store that are in tabular form, and the step of selectively manipulating the records into a data cube may comprise selectively joining and projecting records from the first data store and creating a data cube comprising a table of records.

The data cube allows the present system to aggregate the records in an efficient format such that all new records can be viewed shortly after posting. Further, the unique population identifiers allow users to follow patients over time yielding important results unavailable in other databases, such as patient drug switching behavior. By linking medical and pharmacy transactions at the patient level, new insights such as indication specific use of drugs and patient comorbidities can be determined.

The report displayed by the system may contain several attributes, such as: market shares geographic information at the national, regional, state and MSA levels; trends over time including annual, quarterly, monthly, and weekly periods; traditional measures such as total, new and refilled prescription counts; source of business such as new prescription starts, switches, and continuing patients; prescriber specialty; patient demographics for age and gender; indication specific use; and patient comorbidities. The system can therefore be used in a number of ways to help make business decisions, such as monitoring new drug launches and marketing campaigns, enhanced sales force targeting, and micro-marketing in select geographic areas or to select customers. Furthermore, the system can be used for forecasting and development of a pharmaceutical marketing strategy including indication-specific product positioning, early warning market share shifts, clinical trial site selection, investigator recruiting, and accurate intelligence on market size and demand.

Other objects, features, and advantages of the present invention will become apparent from the drawings, detailed description of the invention, and the claims, below.

DETAILED DESCRIPTION OF THE INVENTION

With reference to the drawings, in which like numerals represent like elements throughout, FIGS. 1A, 1B, 1C, 1D, 1E, 2A, 2B, and 2C illustrate a high-level combined block/flow diagram for the present invention. These figures represent both the elements of a block diagram for, as well as the steps performed by the system of, the present invention.

Referring to FIGS. 1A, 1B, 1C, 1D, 1E, 2A, 2B, and 2C, the primary processing that takes place in the present invention may be performed by, for example, a high-performance computing system, such as a Sun Microsystems ES10000 computer (at SITE 2). On a periodic basis, such as each day, seven days per week, a computing system at SITE 1 places healthcare claims data at step 103 via a secure connection 190 onto a computer system at SITE 1. This healthcare claims data may include, for example, pharmaceutical, 20 medical, and hospital claims 101 that have been "de-identified" at step 102 (explained in further detail below).

The claims data is de-identified at step 102 before it is sent to SITE 2, which includes applying a unique identifier, encrypting this identifier, and removing specific patient identifying fields. Data is then loaded into database tables (such as an Oracle database) at step 104 that also reside on SITE 2. At step 105, SITE 2 runs all processes for analyzing and consolidating the data and for transforming the resulting Oracle tables into OLAP cubes.

The cube building process may run on a different computer (such as SITE 2). Cubes are modeled using an OLAP product on a desktop computer under, for example, the Windows NT operating system.

The cube deployment process may run on a different computer (such as SITE 3). A computing system at SITE 2 places cubes and metadata files at step 106 via a secure connection to SITE 3. Processes run at step 107 at SITE 3 to place the cube on the production web site and to update the web site pages with the associated metadata.

Figure 3A:
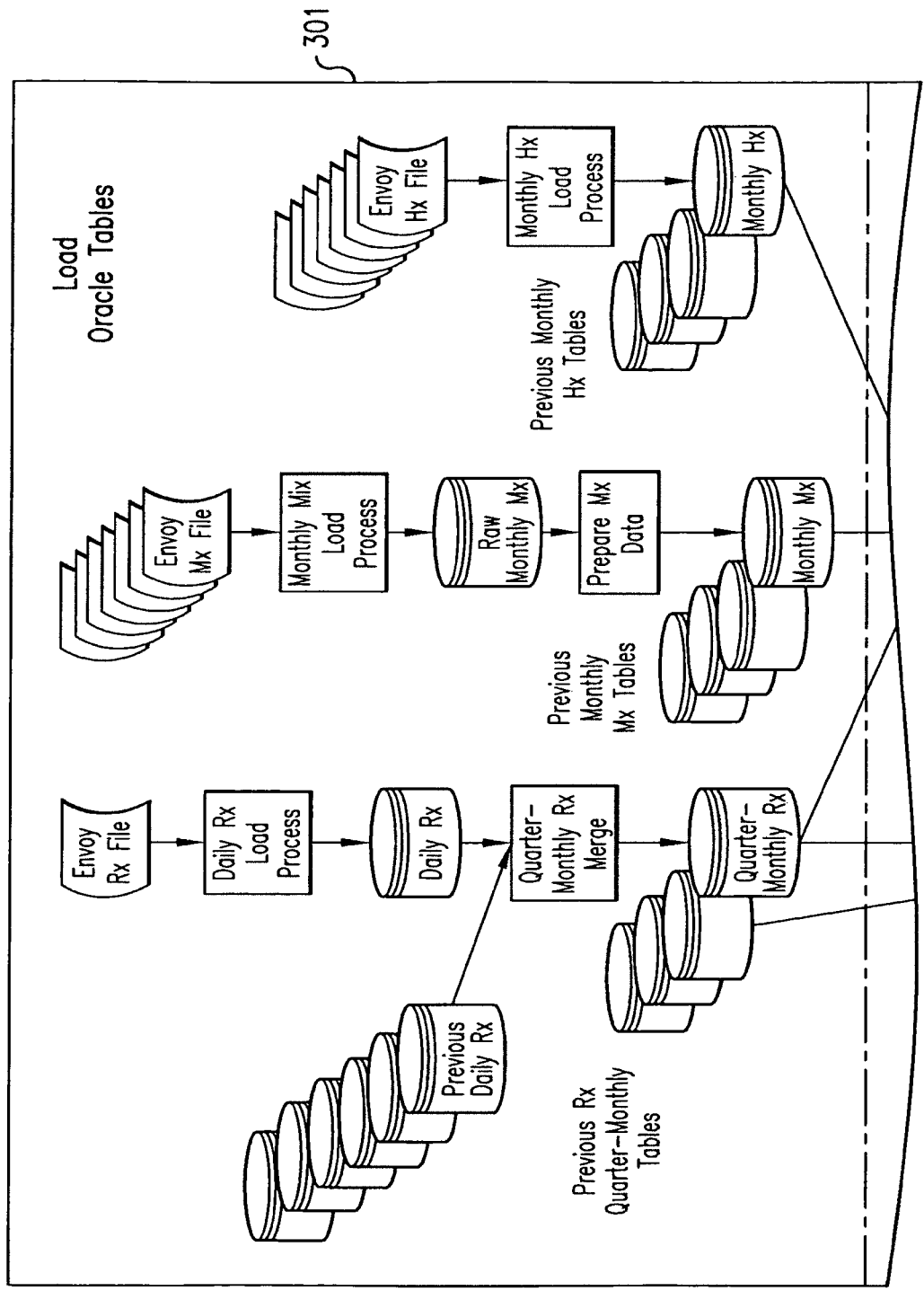
FIGS. 3A, 3B, and 3C illustrate a flow and relationship diagram, showing the overall flow and data relationship of the present invention.
Figure 3B:
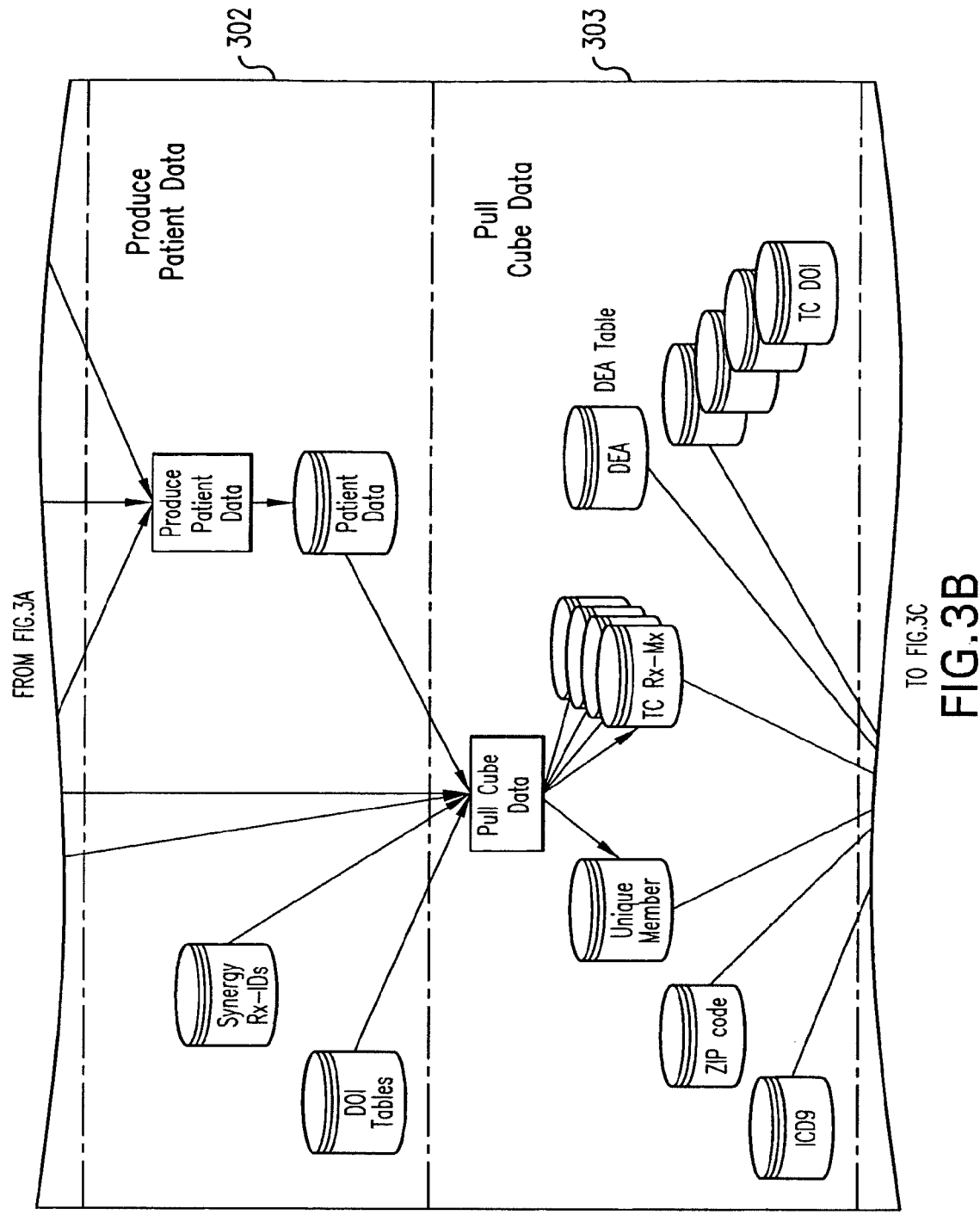
Figure 3C:
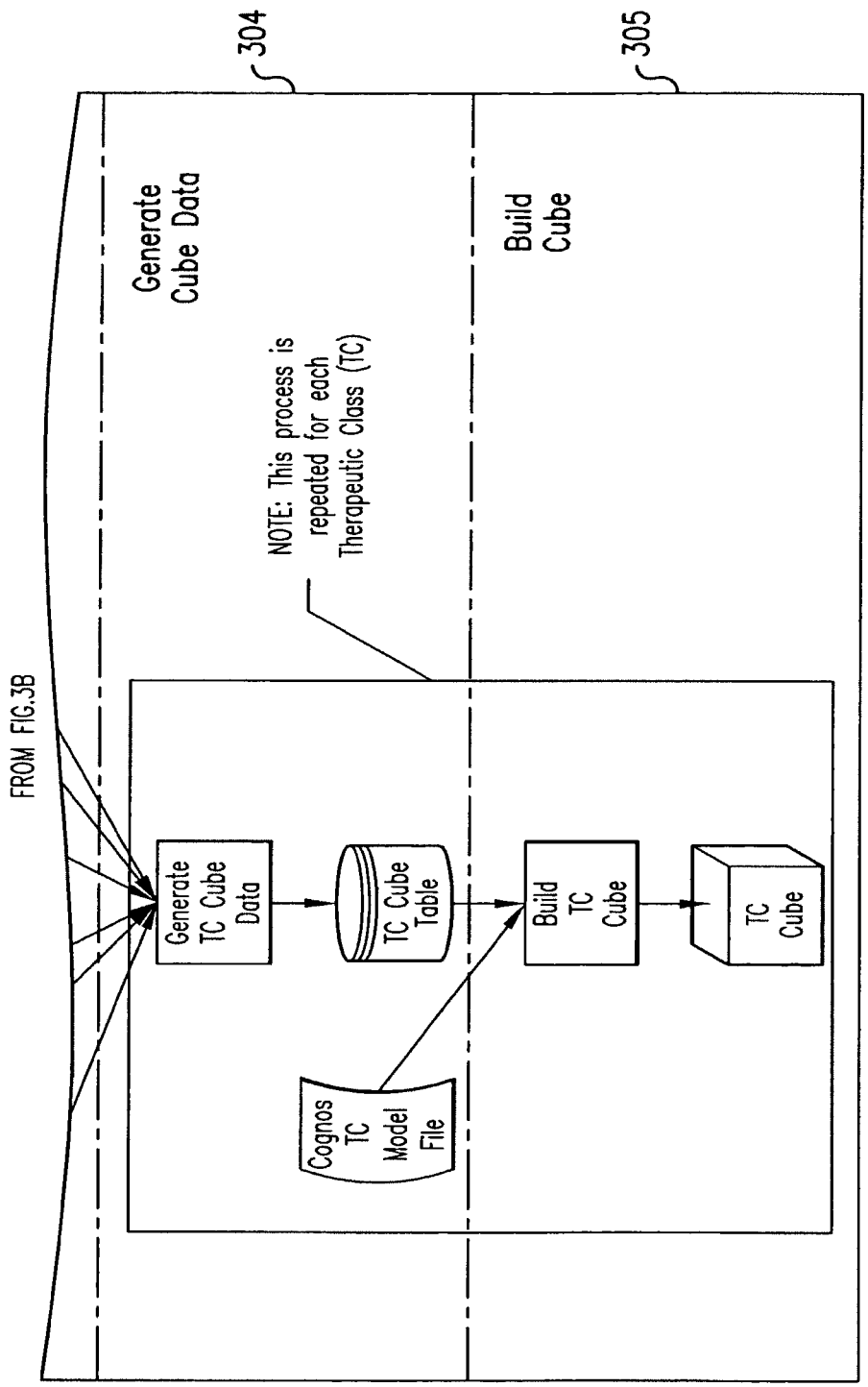

The present process performed at SITE 2 after obtaining data from the SITE 1 computer, making data ready for cube transformers, and then displaying it on the web 5 at SITE 3 can be logically divided into six major steps, as shown in FIGS. 3A, 3B, and 3C.

1. Load Oracle Tables (step 301)
2. Produce Patient Data (step 302)
3. Pull Cube Data (step 303)
4. Generate Cube Data (step 304)
5. Build Cube (step 305)
6. Automated Cube Deployment and Metadata Update Process All these processes are handled, maintained and executed at regular daily, weekly and monthly intervals. There are some processes which are done out of the routine process, such as generation of DOI, zip-state-region, ICD9, etc. tables. FIGS. 3A, 3B, and 3C show a high level overview of the processes used to create cubes.

1. Load Oracle Tables (Step 301)

The Load Oracle Tables process (step 301) can be divided into two logically different steps, daily and monthly processes, described in further detail below with respect to FIGS. 4-8. The daily routines convert the text format data supplied from SITE 1 into "RX" and "Do Not Use Company Name (DNU)" daily Oracle tables. The monthly processes convert Hospital (HX) and Medical (MX) data into monthly Oracle tables. Note that all run times provided below correspond to approximate run times.

1.1 Daily Rx Load Process 401

Figure 4:
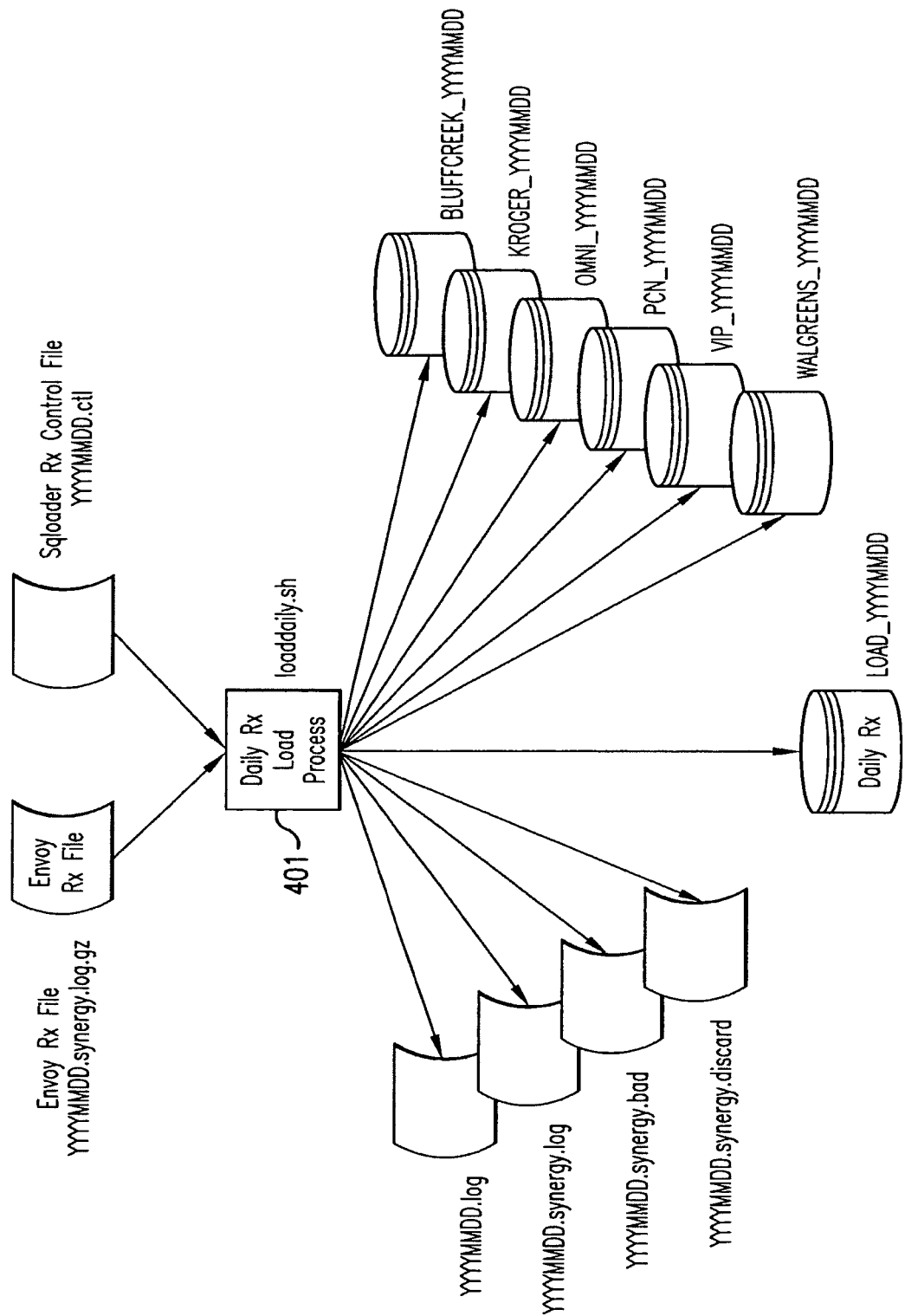
FIG. 4 illustrates the operation of the Daily Rx Load Process of the present invention.

The Daily Rx Load Process 401 is described below with respect to FIG. 4:

| | |
|---|---|
| Script Use | Loaddaily.sh is the unix shell script that uses the SQL Loader Rx Control File to Convert the Rx Text File from SITE 1 into LOAD_YYYYMMDD, {DNU}_YYYY MMDD Oracle tables after doing all the necessary number, char and date conversions. The {DNU} list contains BLUFFCREEK, KROGER, OMNI, PCN, VIP and WALGREENS. |
| Input | YYYYMMDD.synergy.log.gz, RX Control file, YYYYMMDD.ctl. |
| Output | LOAD_19991123, 24 etc. tables for each day of a month. WALGREENS_YYYYMMDD etc. tables for each DNU company. ../log/YYYYMMDD.log ../data.YYYYMMDD.synergy.log ../bad/YYYYMMDD.synergy.bad ../discard/YYYYMMDD.synergy.discard. |
| Frequency | Daily |
| Run Time | ~4 hours |

1.2 Monthly Mx Load Process 501

Figure 5:
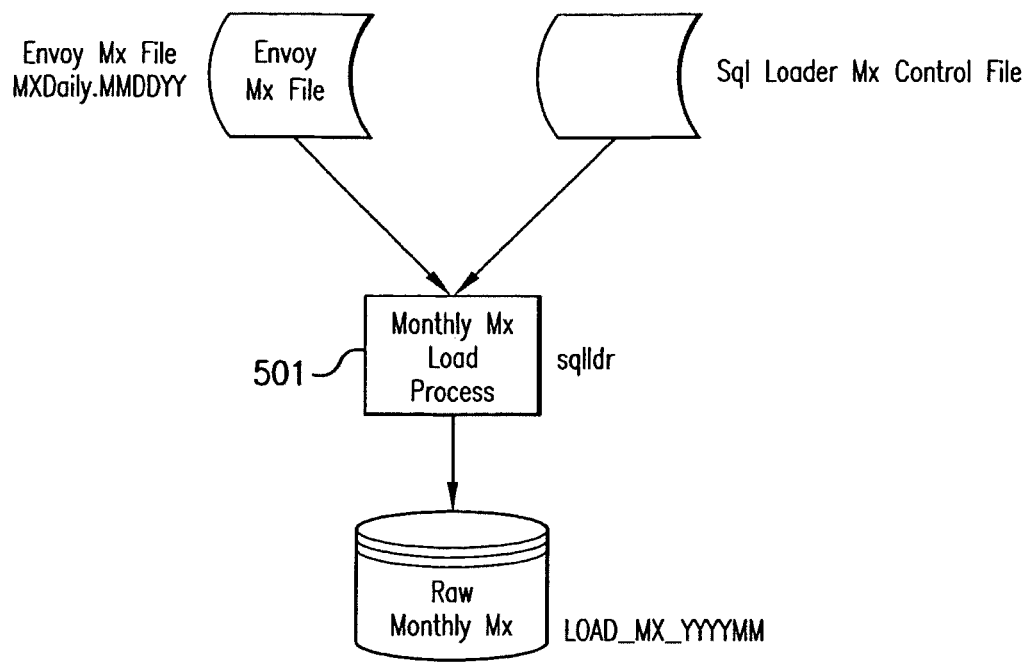
FIG. 5 illustrates the operation of the Monthly Mx Load Process of the present invention.

The Monthly Mx Load Process 501 is described below with respect to FIG. 5:

| | |
|---|---|
| Script Use | SQL LOADER process reads MXDaily.MMDDYY text file and control file to convert it into LOAD_MX_YYYYMM tables. |
| Input | /raid/4011/envoydata/mx/oct1999/data/MXDaily.100199 MX Control file, yyyymmdd.ctl. |
| Output | LOAD_MX_YYYYMM table |
| Frequency | Monthly |
| Run Time | ~8 hours |

1.3 Load HX Text Data 601

Figure 6:
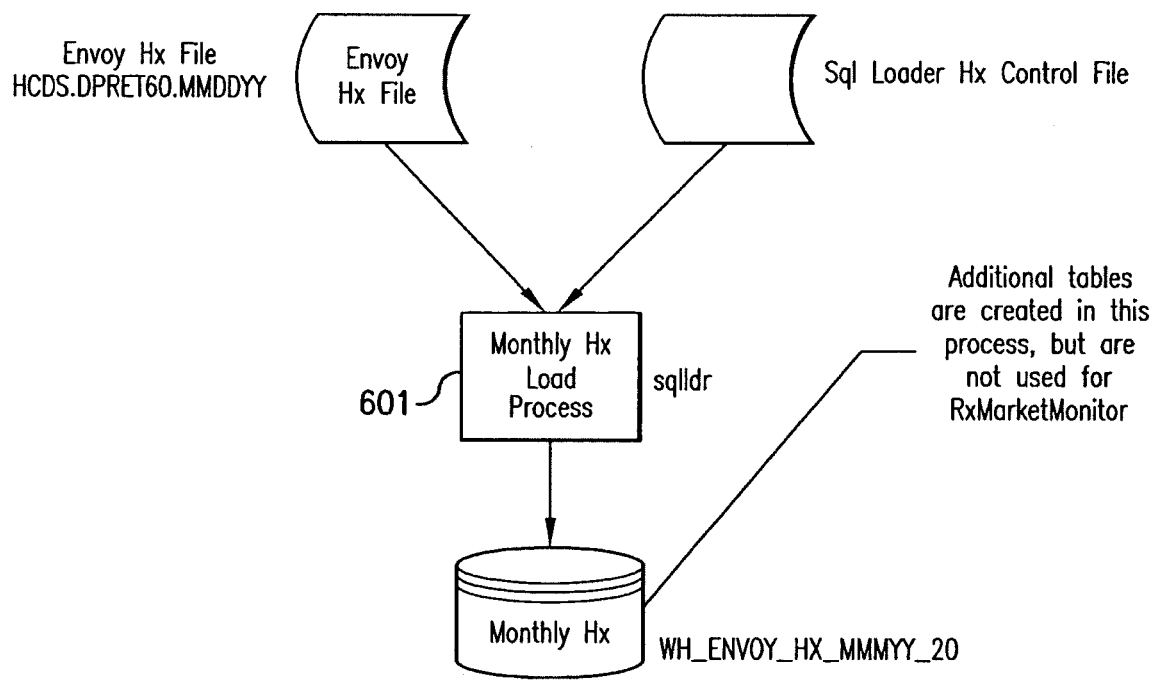
FIG. 6 illustrates the operation of the Monthly Hx Load Process of the present invention.

The Load HX Text Data Process 601 is described below with respect to FIG. 6:

| | |
|---|---|
| Script Use | SQL LOADER process reads MX text file and Control File to convert it into WH_ENVOY_HX_SEP99 tables. |
| Input | /raid/4011/envoydata/hx/sep1999/data/ MCDS.DPRET60.090199, HX Control file, yyyymmdd.ctl. |
| Output | WH_ENVOY_HX_SEP99_10..20..30..36..40..46..50.. 60..61..66..70..80..90 tables for HX. |
| Frequency | Monthly |
| Run Time | ~8 hours |

1.4 Quarter-Monthly Rx Merge 701

Figure 7:
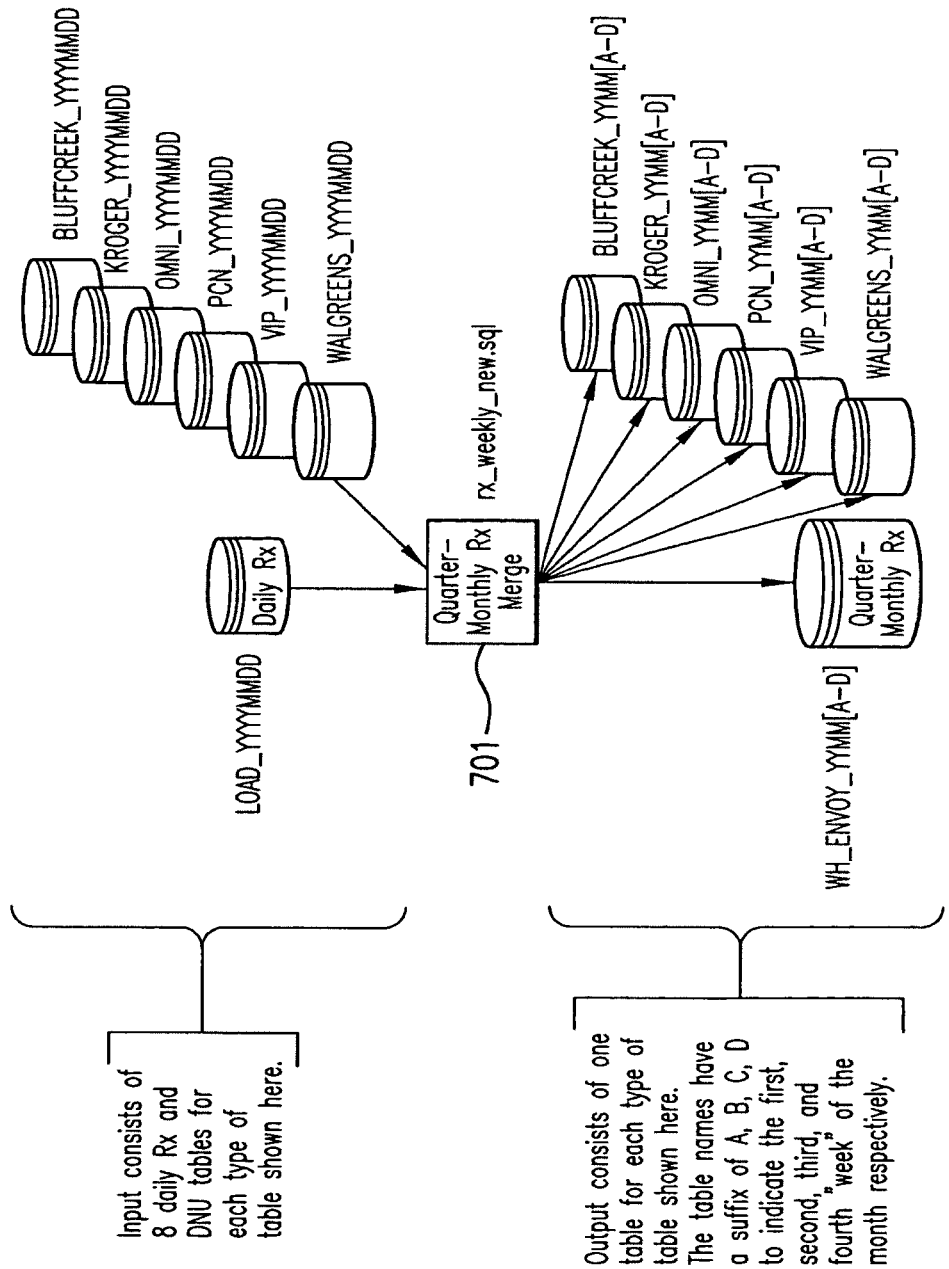
FIG. 7 illustrates the operation of Quarter Monthly Rx Merge Process of the present invention.

The Quarter-Monthly Rx Merge Process 701 is described below with respect to FIG. 7:

| | |
|---|---|
| Script Use | This process uses RX_Weekly_New.sql SQL script to combine all the daily (approx.. 8 days of tables) RX and DNU tables into quarter-monthly tables. |
| Input | LOAD_19991123..24 etc. tables for each day of a month WALGREENS_YYYYMMDD etc. tables for each "DNU" company |
| Output | WH_ENVOY_9911A..B..C..D etc. 4 tables for a month. WALGREENS_9911A..B..C..D like tables for each "DNU" company for a month. |
| Frequency | Monthly |
| Run Time | ~6 hours |

1.5 Prepare Mx Data (801)

Figure 8:
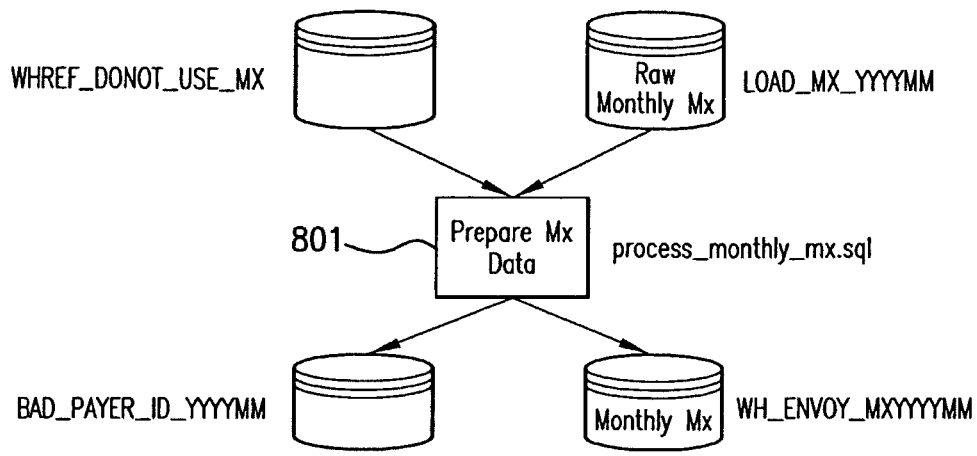
FIG. 8 illustrates the operation of the Prepare Mx Data Process of the present invention.

The Prepare mx Data Process 801 is described below with respect to FIG. 8:

| | |
|---|---|
| Script Use | This process uses Process_Monthly_MX.sql SQL script to validate and convert LOAD_MX_YYYYMM table data into required date, char and numbers. |
| Input | LOAD_MX_YYYYMM, WHREF_DONOT_USE_MX |
| Output | WH_ENVOY_YYYYMM BAD_PAYER_ID_YYYYMM |
| Frequency | Monthly |
| Run Time | |

2. Produce Patient Data (Step 302)

Figure 9:
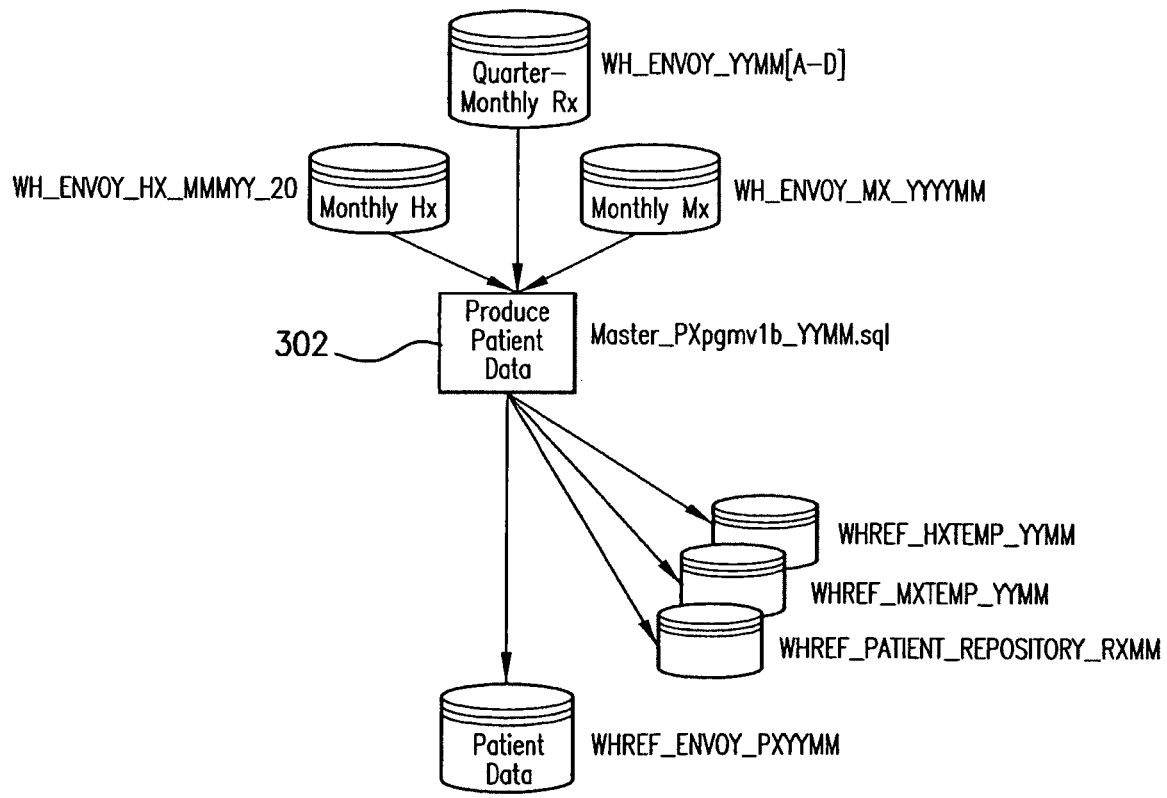
FIG. 9 illustrates the operation of the Produce Patient Data Process of the present invention.

The Produce Patient Data Process of step 302 (FIG. 3B) is described below in further detail with respect to FIG. 9:

| | |
|---|---|
| Script Use | This process uses Master_PXpgmv1b_9910.sql SQL script to combine weekly RX and monthly MX, HX tables to create a relational WHREF_ENVOY_PXYYMM table. |
| Input | WH_ENVOY_YYMMA..B etc., WH_ENVOY_MX_YYYYMM, WH_ENVOY_HX_MMMYY_20 tables. |
| Output | WHREF_PATIENT REPOSITORY RXMM, WHREF_MXTEMP_YYMM, WHREF_HXTEMP_YYMM, WHREF_ENVOY_PXYYMM tables. |
| Frequency | Monthly |
| Run Time | ~13 hours |

3. Pull Cube Data (Step 303)

Figure 10:
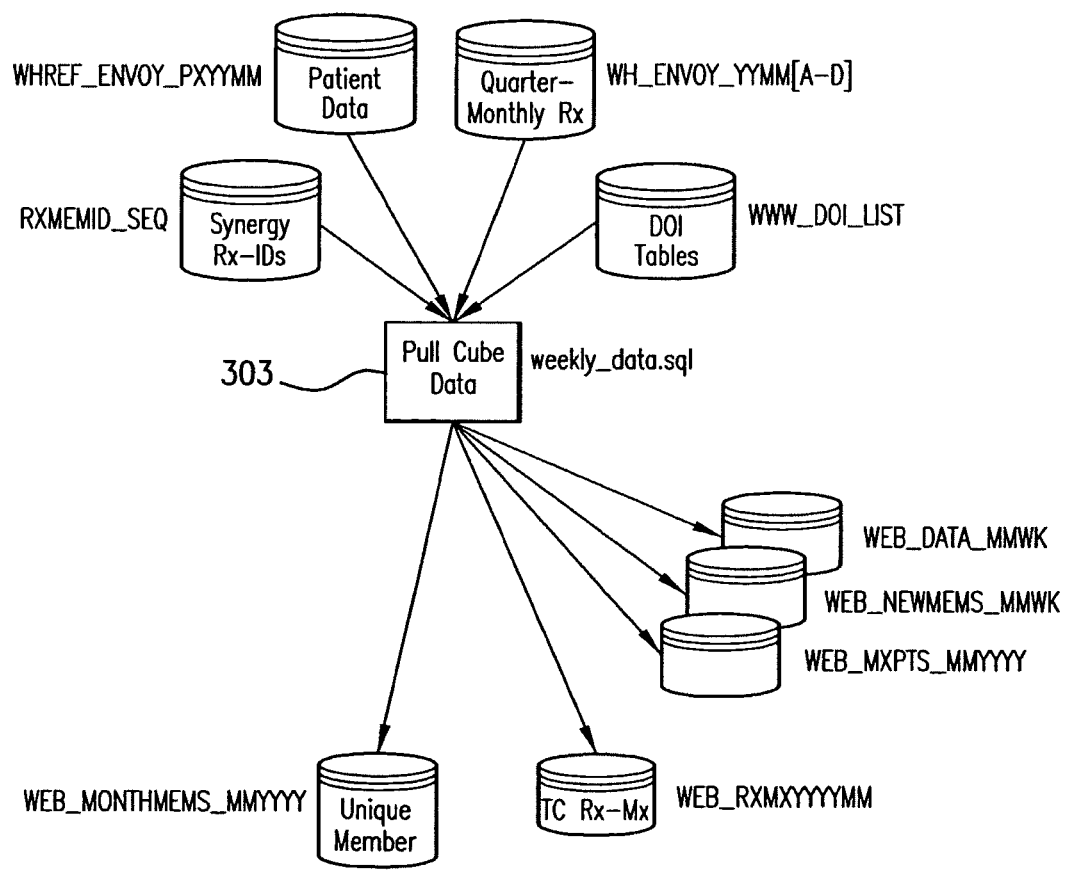
FIG. 10 illustrates the operation of the Pull Cube Data Process of the present invention.

The Produce Patient Data Process of step 303 (FIG. 3B) is described below in further detail with respect to FIG. 10:

This process uses a series of Oracle stored procedures to allow for error checking and audit logging. Logging for these procedures uses the MM_LOG table. These stored procedures are called from the Unix shell using shell script wrappers that input the necessary variable values. The stored procedures used are as follows:

mm00_init mm01_set ears mm02_weekly_data_pull mm03_memids mm04_mx_diags

3.1 Audit Logging in Oracle Table MM_LOG
Structure of the MM_LOG table.

| RUN_DATE | START_TIME | STOP_TIME | CUBE_NAME | PROCESS | RETURN_CODE |
|---|---|---|---|---|---|
| 10-Jul-00 | 8:26:37 | 8:26:38 | | mm00_init( ) | 0 |
| 10-Jul-00 | 8:26:38 | 8:26:;38 | | mm01_set_vars( ) | 0 |
| 11-Jul-00 | 8:26:38 | 12:35:49 | | mm02_weekly_data_pull( ) | 0 |
| 11-Jul-00 | 2:04:59 | 12:11:57 | | mm03_memids( ) | 0 |
| 11-Jul-00 | 1:07:32 | 11:23:46 | | mm04_mx_diags( ) | 1 |

| RUN_DATE | START_TIME | ERROR_CODE | DESCR |
|---|---|---|---|
| 10-Jul-00 | 8:26:37 | Completed | Procedure mm00_init( ) completed successfully |
| 10-Jul-00 | 8:26:38 | Completed | Procedure mm01_set_vars( ) completed successfully |
| 11-Jul-00 | 8:26:38 | Completed | Procedure mm02_weekly_data_pull( ) completed successfully. |
| 11-Jul-00 | 2:04:59 | Completed | Procedure m03_memids( ) completed successfully |
| 11-Jul-00 | 1:07:32 | −904 | ORA-00904: invalid column name |

A record is added to MM_LOG for each process. The name of the process is in the PROCESS column. For cube specific processes, the name of the cube is in the CUBE_NAME column. When a process successfully completes, the RETURN_CODE column contains a 0; when there is an error, the RETURN_CODE column contains a 1.

3.2 Initialization

| | |
|---|---|
| Script Use | The mm00_init procedure initializes the environment for weekly Market Monitory cube processing. The mmOO.sh shell script calls the mm00_init procedure. |
| Input | None |
| Output | MM_LOG table truncated. MM_VARS table truncated. CUBE_DATA_TEXT table truncated. MM_LOG table—row inserted showing successful completion or error condition. |

3.3 Set Variables

| | | |
|---|---|---|
| Script Use | The mm01_set_vars procedure sets variables for the Rx Market Monitor weekly cube processing. The mm01.sh shell script calls the mm01_set_vars procedure with input variables set as text. The mm00_init procedure must already have been run. | |
| Input | p_run_date | Run date of pull as text 'YYYYMMDD'. |
| | p_start_date | Start date of pull as text 'YYYYMMDD'. |
| | p_end_date | End date of pull as text 'YYYYMMDD'. |
| | p_post_date | Post date of pull as text 'YYYYMMDD. |
| | p_acute_lookback | Acute lookback date as text 'YYYYMMDD'. |
| | p_chronic_lookback | Chronic lookback date as text 'YYYYMMDD''. |
| Output | MM_VARS table - row inserted with this week's values as DATE datatype. | |
| | MM_VARS_HIST table - row inserted with this week's values as DATE datatype. | |
| | MM_LOG - row inserted showing successful completion or error condition. | |

3.4 Pull Weekly Data

| | | |
|---|---|---|
| Script Use | The mm02_weekly_data_pull procedure pulls one week of Rx data for weekly Rx Market Monitor cube processing. The mm02.sh shell script calls this procedure with the tablespace variable input set. The mm00_init and mm01_set_vars procedures must already have been run. | |
| Input | p_tablespace | Tablespace name as text. |
| | MM_VARS table | |
| | WH_ENVOY_YYMM where YYMM is the two character year and month from start_date in MM_VARS table. | |
| | WWW_MASTER_DOI | |
| Output | Last week's WEB_DATA_WEEK_PULL table is renamed to WEB_DATA_WEEK_PULL_YYYYMMDD where YYYYMMDD is one day before the start_date in MM_VARS table. New WEB-DATA-WEEK-PULL table is created in the WEB schema in the tablespace named in the p_tablespace parameter. The WEB_DATA_WEEK_PULL table contains Rx data from the start and end dates in the MM_VARS table. | |
| | MM_LOG—a row is inserted to indicate either successful completion or error condition. | |

3.5 Get Memids

| | | |
|---|---|---|
| Script Use | The mm03_memids procedure accumulates six weeks of memids. The mm03.sh shell script calls this procedure and inputs the tablespace parameter. The mm00_init, mm01_set_vars, and mm02_weekly_data_pull procedures must already have been run. | |
| Input | p_tablespace | Tablespace name as text. |
| | MM_VARS table | |
| | ALL_MEM_TO CONVERT table | |
| | WEB_DATA_WEEK_PULL_V2 table | |

-continued

| | |
|---|---|
| | WEB__UMEMS__WEEK__V2__MONDD table where MONDD is the end__date from MM__VARS table as text. WEB__UMEMS__WEEK__V2__MONDD[1-5] tables where MONDD[1-5] are the previous five weeks of data. RXMEMID SEQ table |
| Output | WEB__UMEMS__WEEK__V2__MONDD table is created where MONDD is start__date in MM__VARS table minus one day. WEB__UMEMS__WEEK__PULL is created with data for current week and previous 5 weeks. MM__LOG—a row is inserted to indicate either successful completion or error condition. |

3.6 Get Mx Diagnoses

| | |
|---|---|
| Script Use | The mm04__mx__diags procedure gets diagnoses information from Mx tables for weekly processing. The mm04.sh shell script executes this procedure with the tablespace input variable set. The mm00__init, mm01__set__vars, mm02__weekly__data__pull, and mm03__memids procedures must already have been run. |
| Input | p__tablespace       Tablespace name as text. MM__VARS table WEB__UMEMS__WEEK__PULL__V2 table MASTER PX table WEB__MXPTS__WEEK__PULL__V2 table WH__ENVOY__MX__YYYYMM[1-3] tables where YYYYMM[1-3] are the current month and two prior months of data. WEB__RXMX__WEEK__PULL__V2 table RXMEMID__SEQ table |
| Output | ACUTE__RXMX table—records from the week are appended. CHRONIC__RXMX table—records from the week are appended. MM__LOG table—row inserted to indicate either successful completion or error condition. |

4. Generate TC Cube Data (Step 304)

Figure 11:
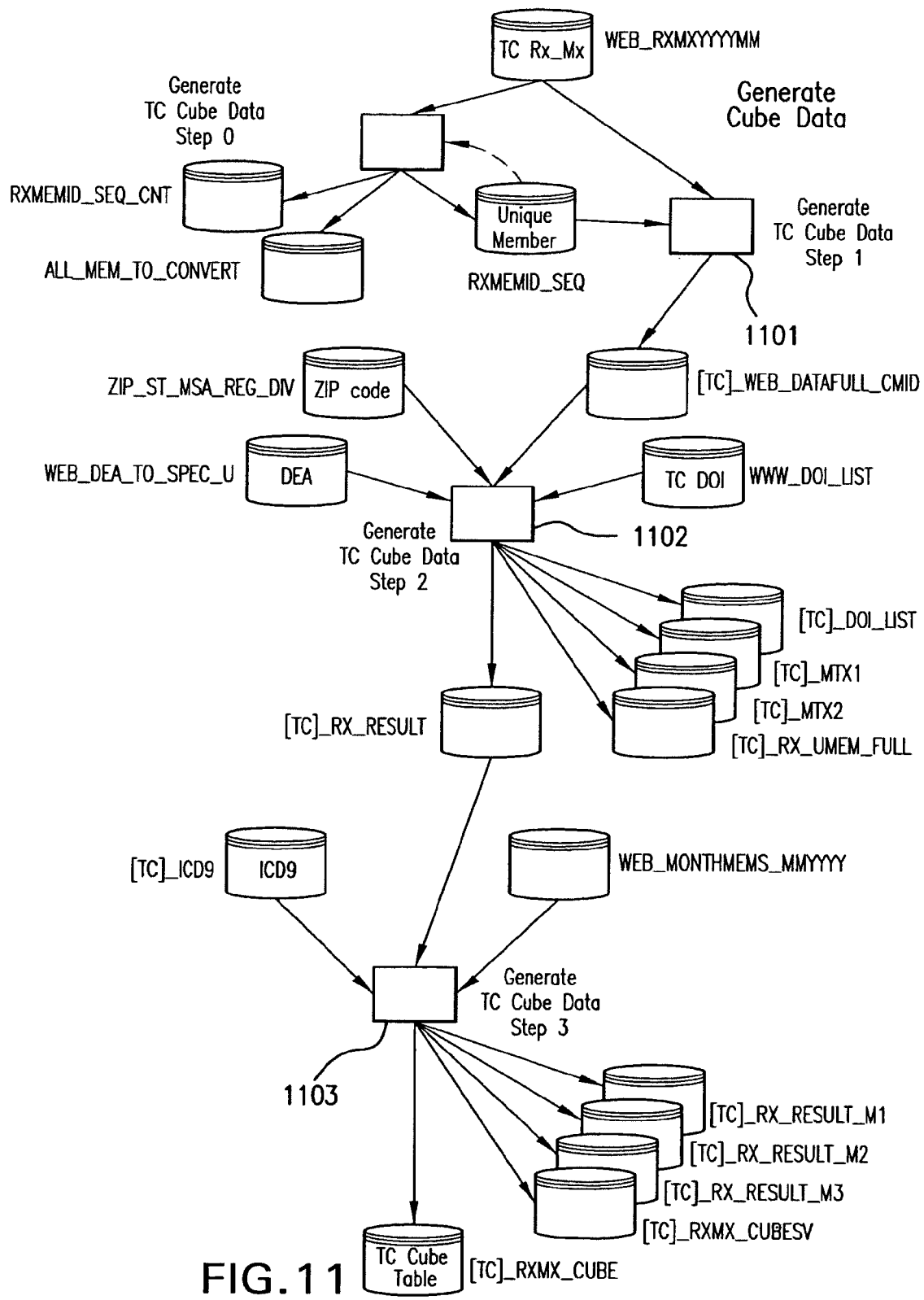
FIG. 11 illustrates the operation of the Generate TC Cube Data Process of the present invention.

The Generate TC Cube Data Process of step 304 (FIG. 3C) is described below in further detail with respect to FIG. 11:

The Generate TC Cube Data Process 304 uses three Oracle stored procedures to generate a cube table which will be further used by data transformers to build a COGNOS readable multi-dimensional formatted cube structure. The last stored procedure updates statistics for each cube. The stored procedures are as follows:

mm05_step1
mm06_step2
mm07_step3
mm08_cube metadata

4.1 Process Step 1101 (Step 1)

| | |
|---|---|
| Script Use | The mm05__step1 procedure must be run for each therapeutic class. This procedure inserts records into the CMID__V2__CLASS table where CLASS is the p__class specified. The mm00__init, mm01__set__vars, mm02__weekly__data__pull, mm03__memids, and mm04__mx__diags procedures must already have been run. |
| Input | p__class       Class name. p__tablespace       Tablespace name as text. p__lookback       Number of days of lookback p__condition       "ACUTE" or "CHRONIC" MM__VARS table WEB__DATA__WEEK__PULL__V2 table CUBE__V2__LIST table CMID__V2__CLASS table where CLASS is the p__class. |
| Output | Records inserted into CMID__V2__CLASS table where CLASS is the p__class. New CMID__V2__CLASS__TMP table is created where CLASS is the p__class. MM__LOG table—row inserted to indicate either successful completion or error condition. |

4.2 Process Step 1102 (Step 2)

| | |
|---|---|
| Script Use | The mm06__step2 procedure must be run for each therapeutic class. This procedure inserts records into the RX__RESULT__V2__CLASS table where CLASS is the p__class specified when the procedure is called. The mm00__init, mm01__set__vars, mm02__weekly__data__pull, mm03__memids, mm04__mx__diags, and mm05__step1 procedures must already have been run. |
| Input | p__class       Class name. p__tablespace       Tablespace name as text. p__lookback       Number of days of look back p__condition       "ACUTE" or "CHRONIC" MM__VARS table CMID__V2__CLASS__TMP table where CLASS is the p__class. CMID__V2__CLASS table where CLASS is the p__class. RX__RESULT__TEMP__CLASS table where CLASS is the p__class. ZIP__ST__MSA__REG__DIV table WEB__DEA__TO__SPEC__U |
| Output | New records are inserted into RX__RESULT__V2__CLASS where CLASS is p__class. MM__LOG table—row inserted to indicate either successful completion or error condition. |

4.3 Process Step 1103 (Step 3)

| | |
|---|---|
| Script Use | The mm07 step3 procedure must be run for each therapeutic class. This procedure creates a new RXMX__CUBE__V2__CLASS table where class is the p__class specified. The mm00__init, mm01__set__vars, mm02__weekly__data__pull, mm03__memids, mm04__mx__diags, mm05__step1, and mm06__step2 procedures must already have been run. |
| Input | p__class       Class name. p__tablespace       Tablespace name as text. p__lookback       Number of days of lookback p condition       "ACUTE" or "CHRONIC" RXMX__CONDITION__V2 table where CONDITION is the p__condition. RX__RESULT__V2__CLASS table where CLASS is the p__class. ICD9 V2__CLASS table where CLASS is the p__class. RX__RESULT__V2__CLASS__M table where CLASS is the p__class. |
| Output | New RXMX__CUBE__V2__CLASS table is created where CLASS is p__class. MM__LOG table—row inserted to indicate either successful completion or error condition. |

4.4 Generate Cube Metadata

| | |
|---|---|
| Script Use | The mm08 cube__metadata procedure must be run for each therapeutic class. This procedure updates the CUBE__DATA table for each cube. The mm00__init, mm01__set__vars, mm02__weekly__data__pull, mm03__memids, mm04__mx__diags, mm05__step1, mm06__step2 and mm07 step3 procedures must already have been run. |
| Input | p__class       Class name. MM__VARS table CUBE__DATA table where CLASS is the p__class. |
| Output | CUBE__DATA__TEXT table is appended where CLASS is p__class. MM__LOG table—row inserted to indicate either successful completion or error condition |

5. Build Cube (Step 305)

Figure 9A:
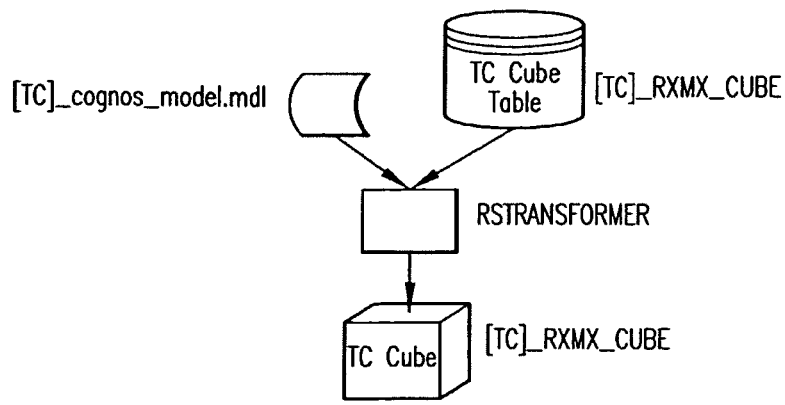
FIG. 9A illustrates the operation of the RSTRANSFORMER process of the present invention.

The Build Cube Process of step 305 (FIG. 3C) is described below in further detail with respect to FIG. 9A:

This process uses a C program to create a cube for each therapeutic class. Each cube is FTP'd to the server of SITE 3. Metadata for each cube is spooled to a text file and FTP'd to the SITE 3 server. The same text files may be concatenated and sent via email to the web developer of SITE 2.

5.1 Build Cube

| | |
|---|---|
| Script Use | The program RSSERVER is repeated for each of the therapeutic classes and called by the script mmv2_'class name'.sh. Data Transformers uses Model Structure and OBES_RX_CUBE Oracle table (built in above process) to finally build a CUBE for each of the therapeutic class. This Cube is then used by COGNOS to show requested information on the Web. |
| Input | OBES_RXMX_CUBE |
| Output | Cube for a OBES Class |
| Frequency | On Request |
| Run Time | ~8 hours |

5.2 FTP Cube to SITE 3 server

| | |
|---|---|
| Script Use | The transfer_mm_cube.sh script renames a cube and puts a copy into directory /raid4011/cubes/transfer where it will automatically be FTP'd to the SITE 3 server. This script is run in parallel for each class (class corresponds to cube). |

5.3 Approve Cube

| | |
|---|---|
| Script Use | The approve_cube script is run manually for each cube after quality assurance has been performed. This script is run in parallel for each class (class responds to cube). |

5.4 Create Metadata text file/FTP to SITE 3 server

| | |
|---|---|
| Script Use | The process gen_mm_file.sql is called by gen_mm_file.sh to spool metadata for a cube to a text file. The text file is put into a directory where it is automatically FTP'd to the SITE 3 server. This script is run in parallel for each class. All procedures to pull cube data must have been successfully completed and the metadata must exist in the Oracle tables cube_data and cube_data_text. |

5.5 E-mail Metadata to Web Developer

| | |
|---|---|
| Script Use | The email_meta.sh script will e-mail metadata to a SITE 2 Web Developer. This script is run in parallel for each class (class corresponds to cube). |

6. Automated Cube Deployment and MetaData Update Process

Automated processes exist on the OnLine Analytical Processing (OLAP) host machine to deploy data cubes (such as QUINTERNET™ Series, from Quintiles Transnational Corp.) to the production web site, cubes ready for Quality Assurance (QA) verification, as well as to automatically update "metadata" on production web pages. This enables production cube deployments and web page updates to occur during off-peak hours without any manual intervention.

As a QUINTERNET™ Series data cube is created, the cube is sent via a secure connection to the host machine. The cube is then automatically "served up" to the QA location on the web, to which only authorized personnel have access.

For each cube approval, a "metadata" file is transmitted from the SITE 2 server, via a secure connection, to the host machine in a specific location (directory within a file system). This secure transmission may occur after a data cube has passed the QA verification.

The metadata file contains statistical information about the specific cube (e.g.—date that cube contains data through, number of records, number of patients, etc.). Several times each night, an automated process may be initiated which checks for the presence of a metadata file and a corresponding data cube file. If matching files for a specific cube exist, the process automatically "serves" up this cube into production for access via the web pages. In addition, the HTML page which contains the metadata for the cube is updated with the metadata contained in the metadata file.

The server at, for example, SITE 3 may prepare and maintain HTML template files for each QUINTERNET™ Series cube. These files contain the base HTML used to create each cube's web page. Instead of the actual metadata values that will populate the cubes' web pages, the HTML template files may contain placeholder tags. These placeholder tags are replaced by data values supplied by SITE 2 in metadata files.

SITE 2 transfers the template files and the metadata files to a host via FTP. The metadata files are transferred to the host each time a cube is approved. Template files are maintained for each QUINTERNET™ Series cube and are updated by SITE 2 as necessary so that a current version of each cube's template file is always available for processing on the host.

After a cube has been updated, reviewed for quality and approved by the operator of SITE 2, SITE 2 transfers a metadata file for that cube to the host via FTP. The metadata files contains the same tags found in the HTML template file for each cube. Each of these tags is coupled with a value that will be substituted for the placeholder tag in the HTML template file.

An event-driven file processing script runs periodically via cron, a unix scheduling system, on the host. If the file processing script detects the existence of a designated flag file, a script called enable_cube.ksh is run. The enable_cube.ksh script calls a Perl script, replaceHtmlMetaTags.pl, passing it the name of the cube being processed and the name of the related metadata file. The enable_cube.ksh script also updates the metadata file with a tag/value pair representing the date the updated cube is being deployed.

Figure 1A:
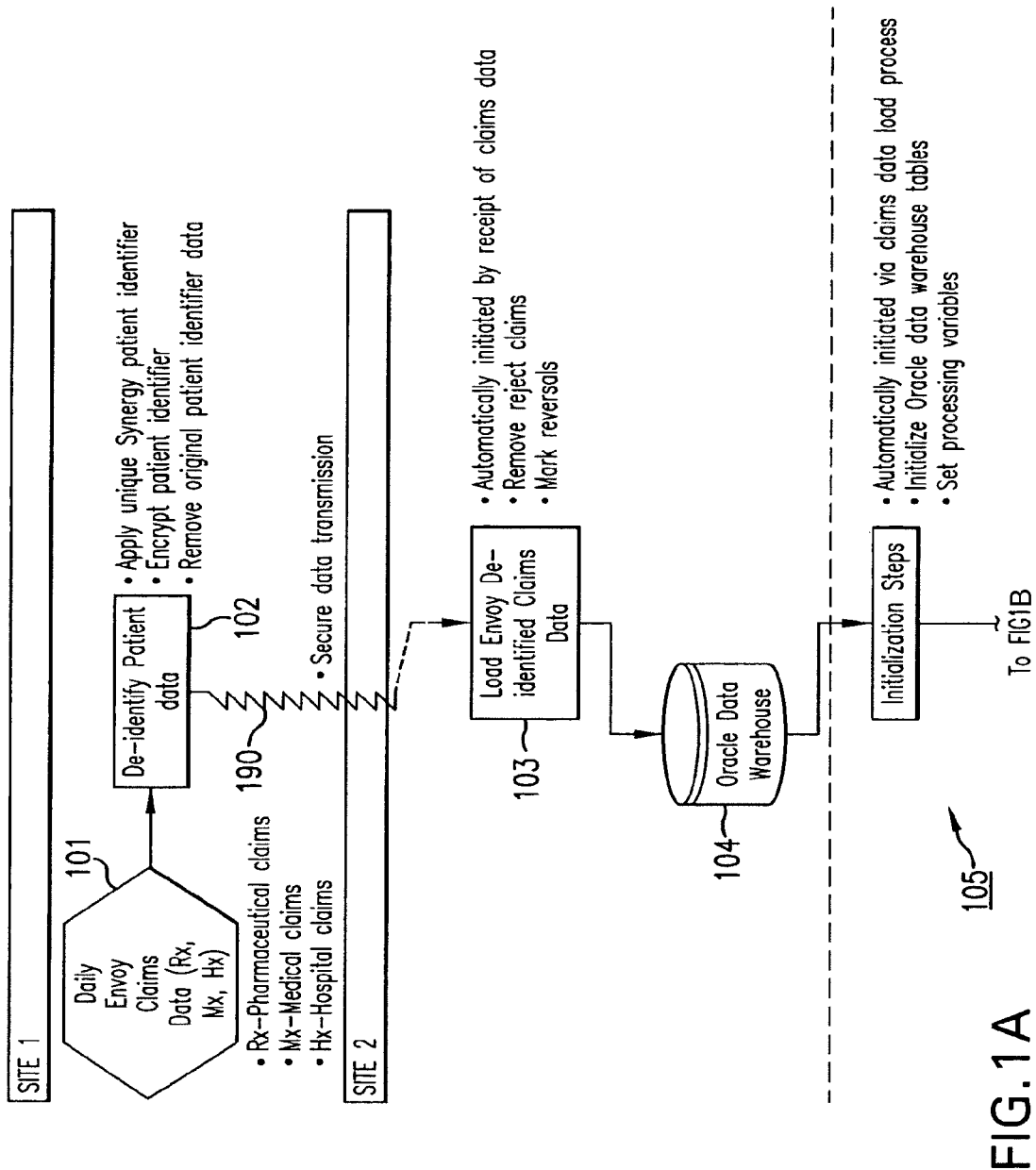
FIGS. 1A, 1B, 1C, 1D and 1E are block and flow diagrams showing the overall structure and overall flow of the present invention in one embodiment.
Figure 1B:
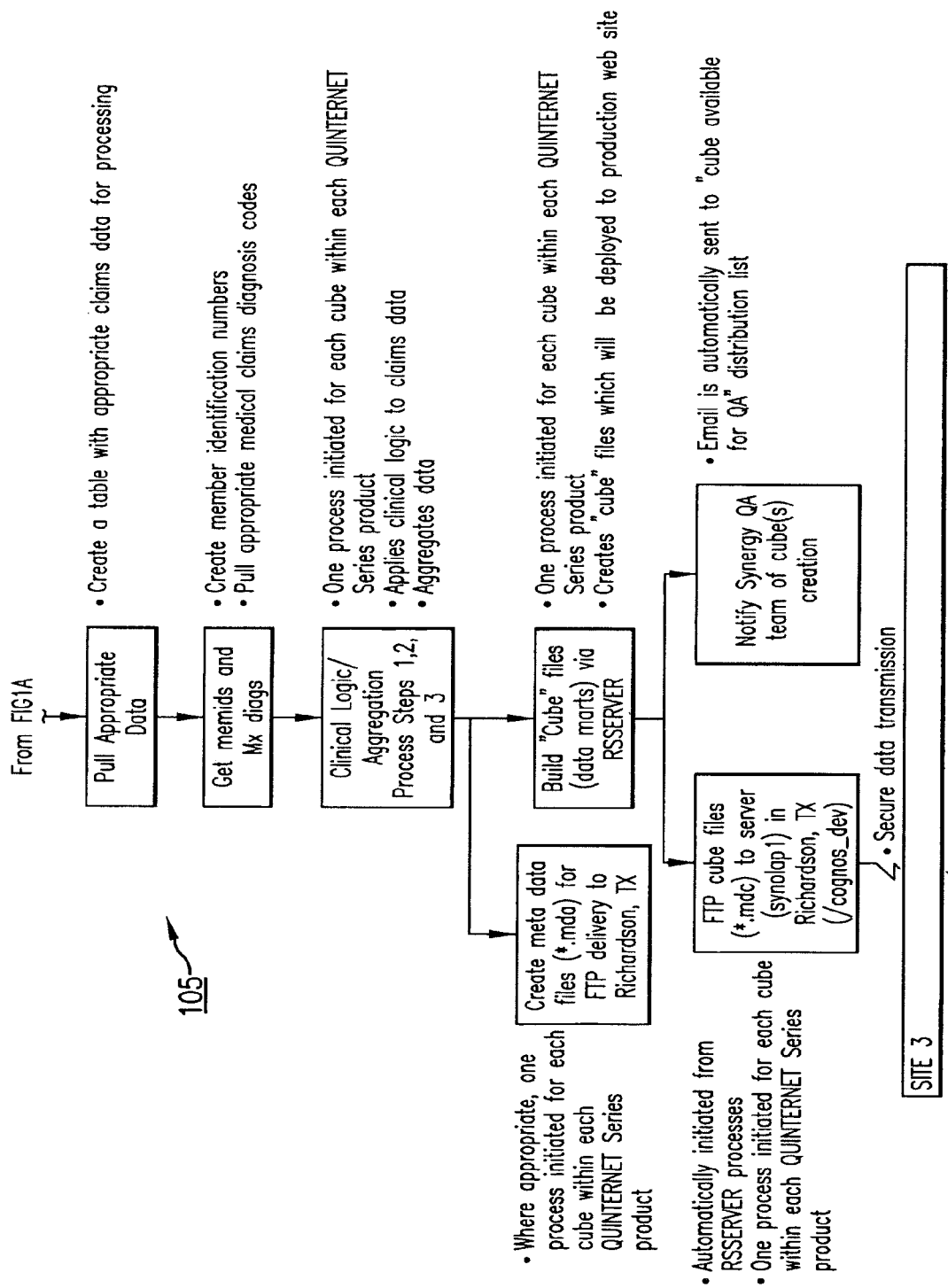
Figure 1C:
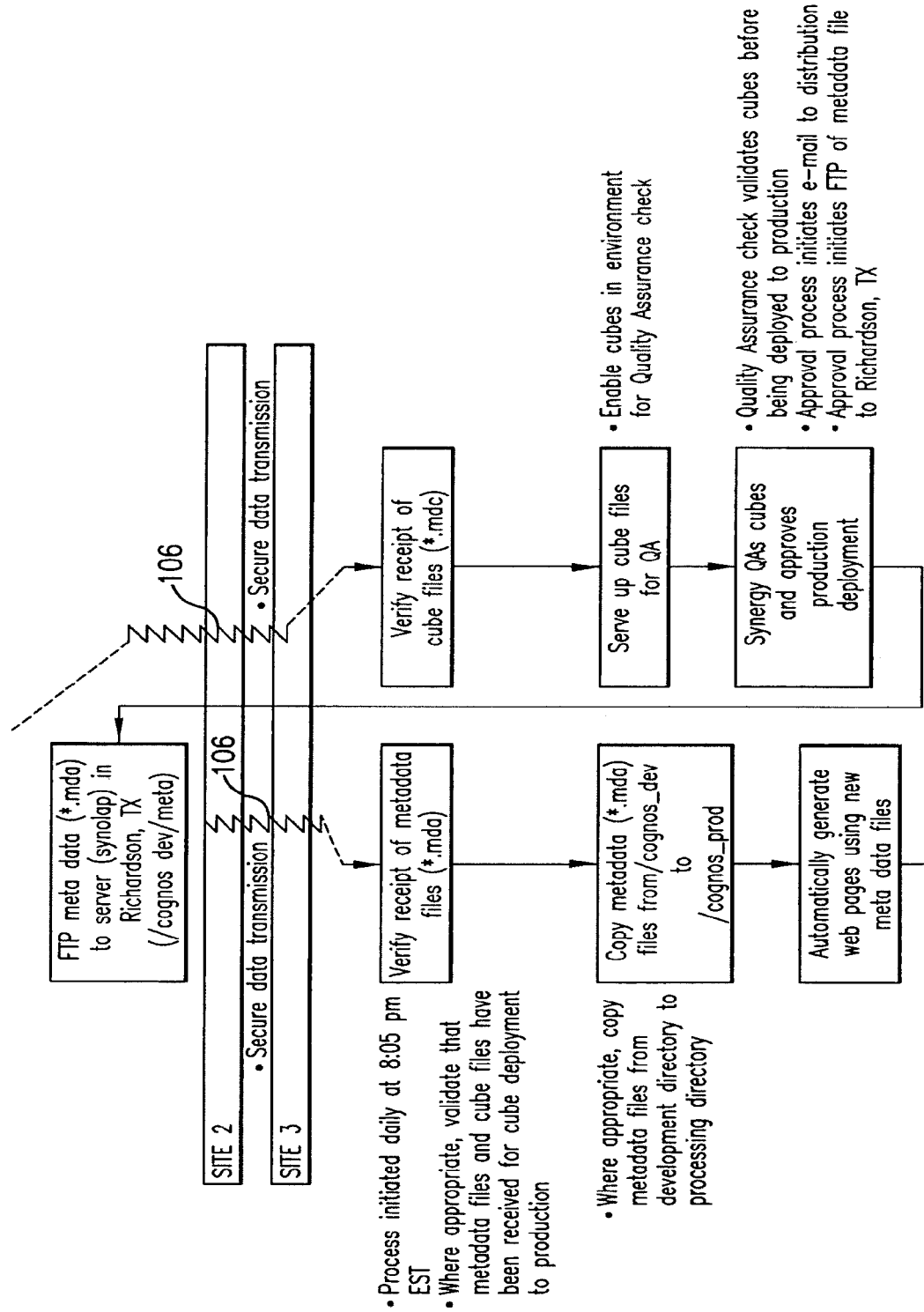
Figure 1D:
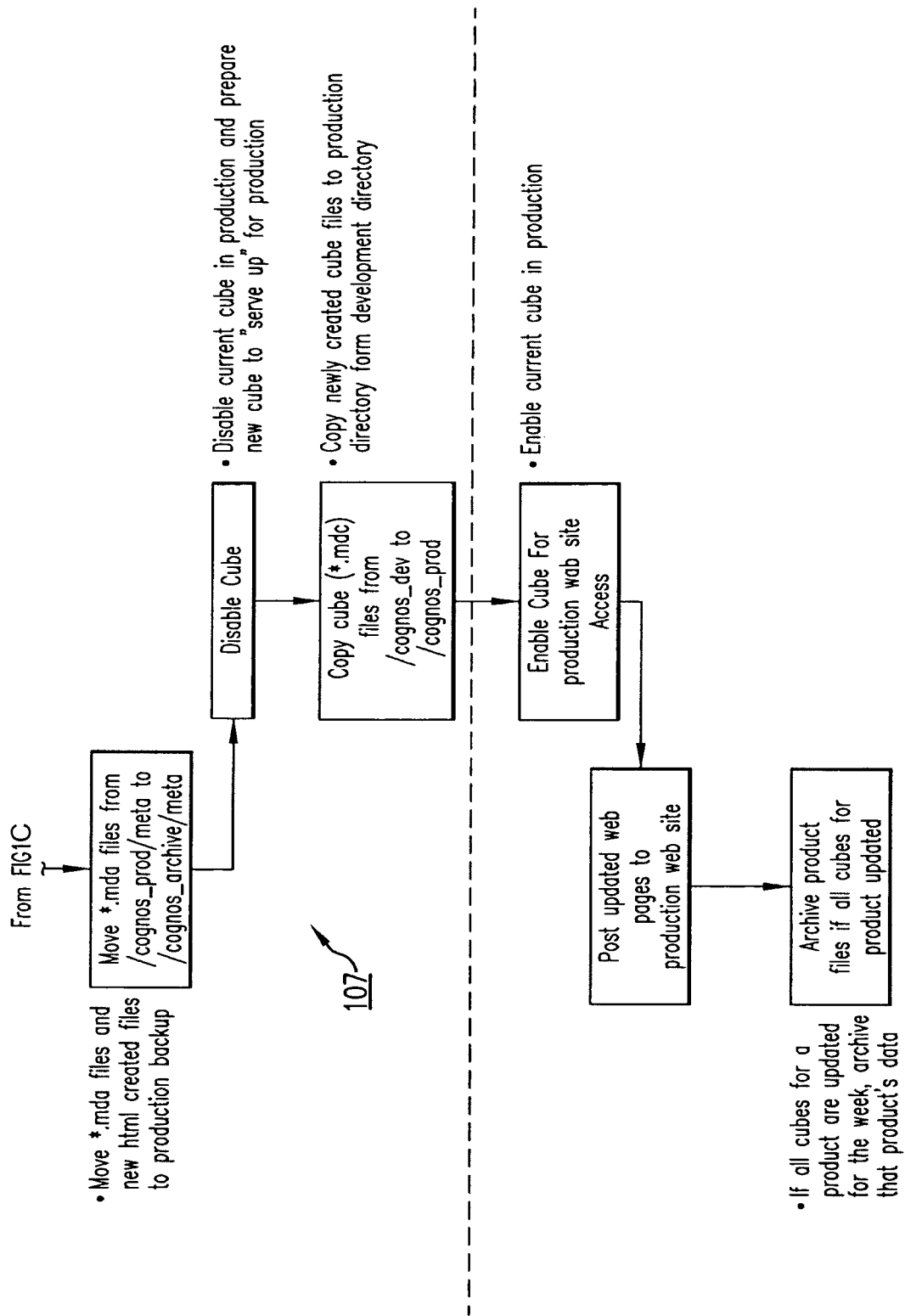
Figure 1E:
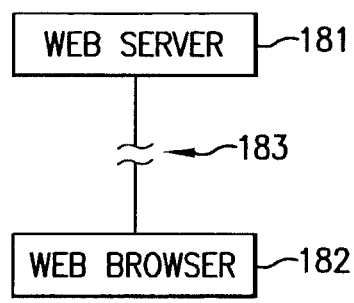
Figure 2A:
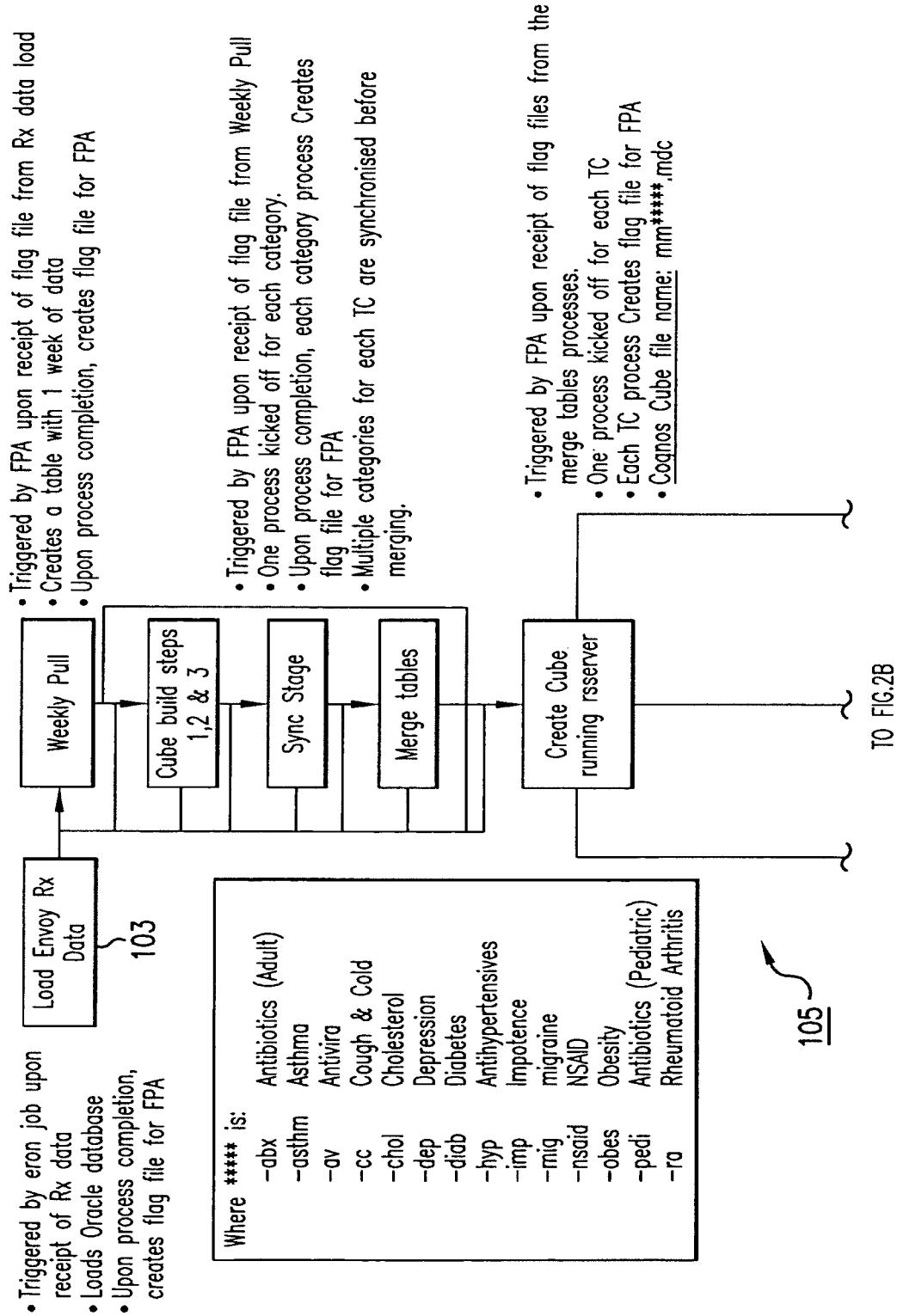
FIGS. 2A, 2B, and 2C are block and flow diagrams showing the overall structure and overall flow of the present invention in one embodiment.
Figure 2B:
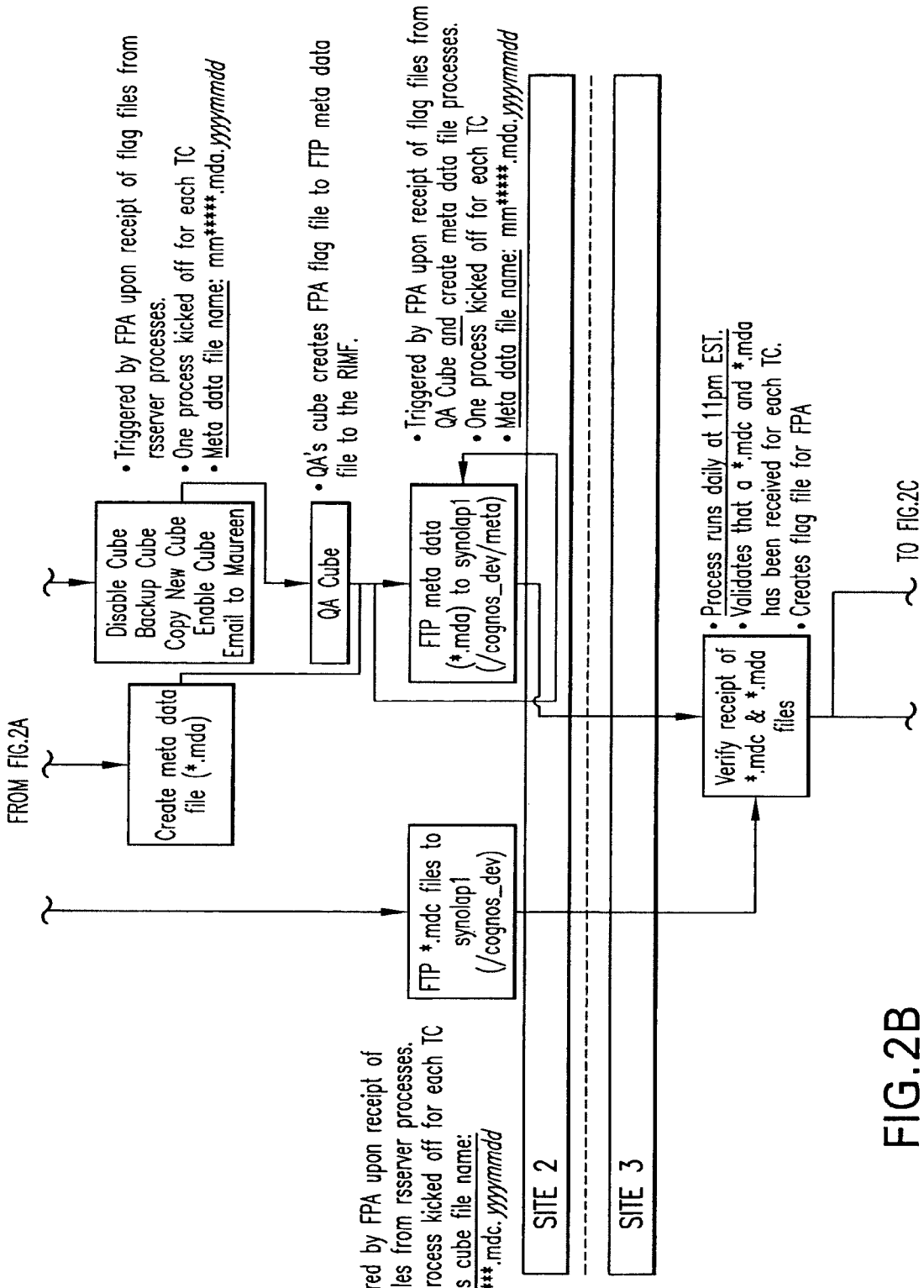
Figure 2C:
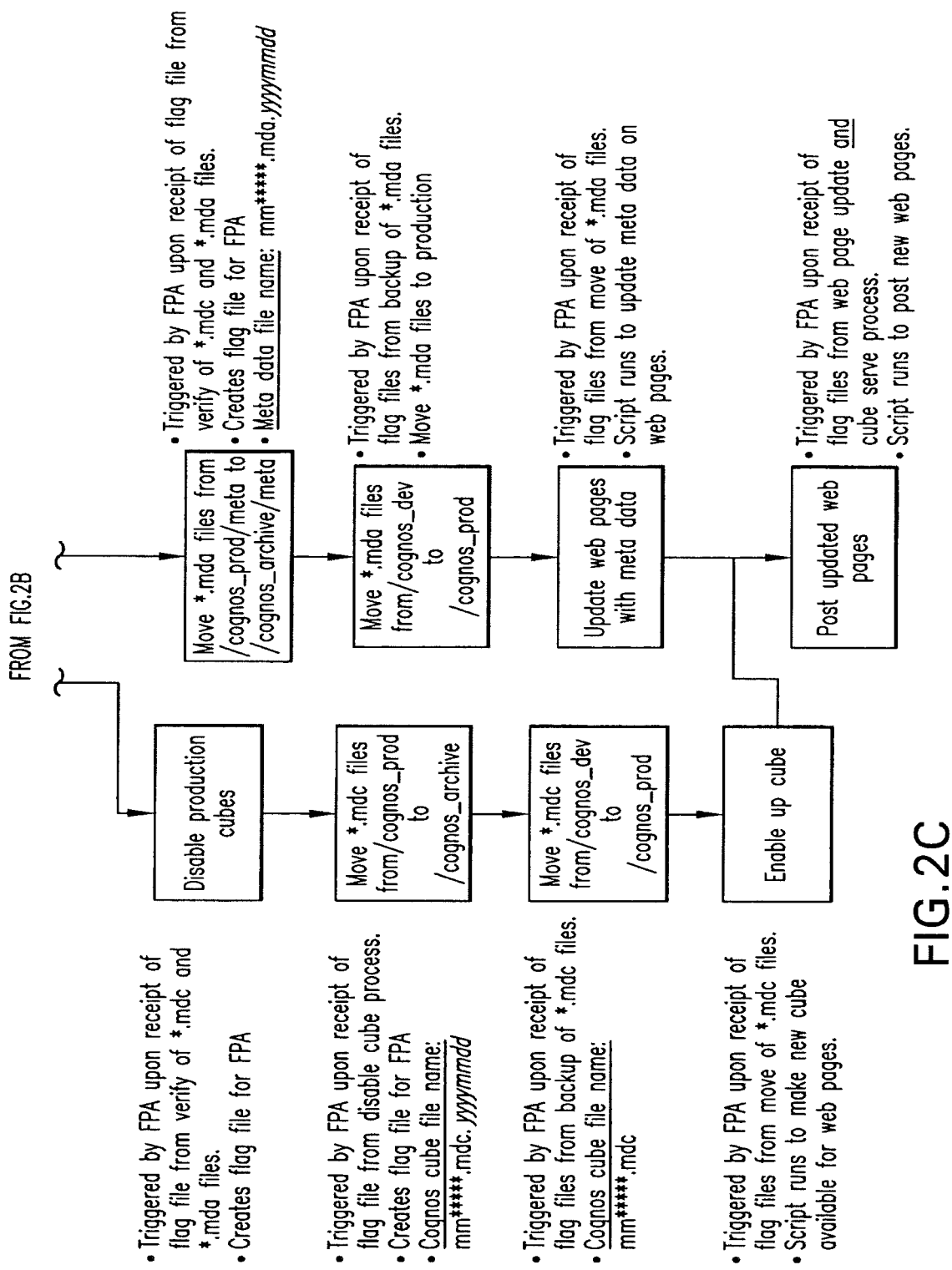

The purpose of the replaceHtmlMetaTags.pl script is to automatically generate HTML pages for the QUINTERNET™ Series products. The replaceHtmlMetaTags.pl script substitutes the values in the metadata file for the placeholder tags in the template and saves the resulting output in an HTML file. Referring to FIG. 1E, the enable_cube.ksh script then promotes the updated HTML file(s) to SITE 3's web server 181 thus making it available via, for example, the Internet 183, to users of web browsers 182 operating on client computers.

The present invention may be implemented with a processing schedule defined in many ways. For example, the schedule may be on a weekly or monthly basis, depending upon the needs of the implementation. At times, special requests may be required and the ability to process data and create cubes on an ad hoc basis exists.

While there has been shown the preferred embodiment of the present invention, it is to be understood that certain changes can be made in the forms and arrangements of the elements of the system and the steps of the method without departing from the spirit and scope of the invention as is set forth in the Claims.

A system for analyzing de-personalized health care data includes health care databases and a processor connected to the health care databases. The health care data bases each include at least one record, and each record includes a depersonalized yet unique patient identifier associated with a patient. The de-personalized patient identifier is common for a specific patient across several health care databases. According to one embodiment, the de-personalized health care data can be pharmaceutical claims data.

The processor performs the steps of: (i) receiving records from the health care databases; (ii) querying the records received from the health care databases, based upon selected person-level criteria; and (iii) generating at least one report based upon the results of the querying step. In another embodiment, the generating step performed by the processor can include the step of manipulating the results for display in specific views that satisfy specific analytical goals. In yet another embodiment, the generating step performed by the processor can include the step of displaying the report in a tabular format.

A method for analyzing de-personalized health care data within health care databases, wherein the health care databases each include at least one record. Each record includes a depersonalized yet unique patient identifier associated with a patient. The de-personalized patient identifier is common for a specific patient across the health care databases. According to one embodiment, the de-personalized health care data includes pharmaceutical claims data. The method includes the steps of: (a) receiving records from the health care databases; (b) querying the records received from the health care databases; and (c) generating at least one record based upon the results of the querying step. In one embodiment, the generating step includes the step of manipulating the results for display in specific views that satisfy specific analytical goals. In another embodiment, the generating step includes the step of displaying the report in a tabular format.

The invention claimed is:

1. A system for de-identifying health care data, comprising:
   at least one health care database, the at least one health care database including at least one patient record, each patient record including a plurality of identification fields associated with a patient and at least one health care field, wherein at least one subset of the identification fields associated with a patient uniquely identifies the patient; and
   one or more processors in communication with the at least one health care database and a second database, wherein the one or more processors execute instructions that cause the one or more processors to:
      select a patient record from the at least one health care database,
      access a plurality of the identification fields included in the patient record, the accessed plurality of identification fields uniquely identifying the patient,
      concatenate, into a string, information from each of the accessed plurality of identification fields included in the patient record,
      generate an encrypted unique patient identifier by encrypting the concatenated string of information,
      generating a de-identified patient record, wherein the de-identified patient record includes the at least one health care field that is included in the selected patient record and the encrypted unique patient identifier, and wherein the de-identified patient record does not include any information that identifies the patient other than the encrypted unique patient identifier, and
      transmit the de-identified patient record to the second database.

2. The system of claim 1, wherein the at least one health care field that is included in the selected patient record comprises pharmaceutical claims data, medical claims data, or hospital claims data.

3. The system of claim 1, wherein the one or more processors execute instructions that cause the one or more processors to:
   identify one or more records stored in the second database that include the encrypted unique patient identifier, and
   generate a report based on data included in the identified records.

4. The system of claim 1, wherein the plurality of identification fields included in the selected patient record include one or more of a patient's name, address, social security number, birthday, or gender.

5. A method for de-identifying health care data comprising:
   selecting, by one or more processors, a patient record from at least one health care database, wherein the at least one health care database includes at least one patient record, each patient record including a plurality of identification fields associated with a patient and at least one health care field, and wherein at least one subset of the identification fields associated with a patient uniquely identifies the patient;
   accessing a plurality of the identification fields included in the patient record, the accessed plurality of identification fields uniquely identifying the patient;
   concatenating, into a string, information from each of the accessed plurality of identification fields included in the patient record;
   generating an encrypted unique patient identifier by encrypting the concatenated string of information;
   generating a de-identified patient record, wherein the de-identified patient record includes the at least one health care field that is included in the selected patient record and the encrypted unique patient identifier, and wherein the de-identified patient record does not include any information that identifies the patient other than the encrypted unique patient identifier; and
   transmitting the de-identified patient record to the second database.

6. The method of claim 5, wherein the at least one health care field that is included in the selected patient record comprises pharmaceutical claims data, medical claims data, or hospital claims data.

7. The method of claim 5 further comprising:
   identifying one or more records stored in the second database that include the encrypted unique patient identifier; and
   generating a report based on data included in the identified records.

8. The method of claim 5, wherein the plurality of identification fields included in the selected patient record include one or more of a patient's name, address, social security number, birthday, or gender.

9. A non-transitory computer-readable medium encoded with instructions that, when executed by one or more processors, cause the one or more processors to perform operations comprising:
   selecting a patient record from at least one health care database, wherein the at least one health care database includes at least one patient record, each patient record including a plurality of identification fields associated with a patient and at least one health care field, and wherein at least one subset of the identification fields associated with a patient uniquely identifies the patient;
   accessing a plurality of the identification fields included in the patient record, the accessed plurality of identification fields uniquely identifying the patient;
   concatenating, into a string, information from each of the accessed plurality of identification fields included in the patient record;
   generating an encrypted unique patient identifier by encrypting the concatenated string of information;

generating a de-identified patient record, wherein the de-identified patient record includes the at least one health care field that is included in the selected patient record and the encrypted unique patient identifier, and wherein the de-identified patient record does not include any information that identifies the patient other than the encrypted unique patient identifier; and transmitting the de-identified patient record to the second database.

10. The computer-readable medium of claim 9, wherein the at least one health care field that is included in the selected patient record comprises pharmaceutical claims data, medical claims data, or hospital claims data.

11. The computer-readable medium of claim 9, further comprising:

identifying one or more records stored in the second database that include the encrypted unique patient identifier; and generating a report based on data included in the identified records.

12. The computer-readable medium of claim 9, wherein the plurality of identification fields included in the selected patient record include one or more of a patient's name, address, social security number, birthday, or gender.

* * * * *